United States Patent
Kende et al.

(10) Patent No.: US 6,713,059 B2
(45) Date of Patent: Mar. 30, 2004

(54) ANTIBODIES RAISED AGAINST IMMUNOGENIC CONJUGATES OF GRAM-NEGATIVE BACTERIAL AUTOINDUCER MOLECULES

(75) Inventors: Andrew S. Kende, Pittsford, NY (US); Barbara H. Iglewski, Fairport, NY (US); Roger Smith, Rochester, NY (US); Richard P. Phipps, Pittsford, NY (US); James P. Pearson, Cambridge, MA (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 10/121,207

(22) Filed: Apr. 11, 2002

(65) Prior Publication Data

US 2003/0095985 A1 May 22, 2003

Related U.S. Application Data

(62) Division of application No. 09/293,687, filed on Apr. 16, 1999, now Pat. No. 6,395,282.
(60) Provisional application No. 60/082,025, filed on Apr. 16, 1998.

(51) Int. Cl.$^7$ ..................... A61K 39/40; A61K 39/395; G01N 33/53; C07K 16/00
(52) U.S. Cl. ............................. 424/150.1; 424/139.1; 424/141.1; 424/163.1; 424/170.1; 424/169.1; 424/175.1; 435/975; 530/388.2; 530/388.4; 530/388.1; 530/388.9; 530/389.5
(58) Field of Search ..................... 530/388.2, 388.4, 530/388.1, 388.9, 389.5; 435/975; 424/139.1, 141.1, 150.1, 163.1, 170.1, 169.1, 175.1

(56) References Cited

U.S. PATENT DOCUMENTS

| 4,673,574 A | 6/1987 | Anderson ............... 424/92 |
| 5,591,872 A | 1/1997 | Pearson et al. ........... 549/321 |
| 5,593,827 A | 1/1997 | Bycroft et al. ............ 435/6 |
| 6,194,178 B1 | 2/2001 | Palcic et al. ............. 435/84 |

OTHER PUBLICATIONS

Bever et al., "Molecular Characterization and Nucleotide Sequence of the *Pseudomonas aeruginosa* Elastase Structural Gene," *J. Bacteriol.* 170:4309–4314 (1988).

Iglewski et al., "*Pseudomonas aeruginosa* Exoenzyme S: An Adenosine Diphosphate Ribosyltransferase Distinct From Toxin A," *Proc. Natl. Aca. Sci. USA* 75:3211–3215 (1978).

Iglewski, et al., "NAD–Dependent Inhibition of Protein Synthesis by *Pseudomonas aeruginosa* Toxin," *Proc. Natl. Acad. Sci. USA* 72:2284–2288 (1975).

Kessler et al., "Synthesis, Processing and Transport of *Pseudomonas aeruginosa* Elastase," *J. Bacteriol.* 170:5241–5247 (1988).

Latifi et al., "A Hierarchical Quorum–Sensing Cascade in *Pseudomonas aeruginosa* Links the Transcriptional Activators LasR And RhlR (VsmR) to Expression of the Stationary–Phase Sigma Factor RpoS," *Mol. Microbiol.* 21:1137–1146 (1996).

Pesci et al., "Regulation of las and rhl Quorum Sensing in *Pseudomonas aeruginosa*," *J. Bacteriol.* 179:3127–3132 (1997).

Schneerson et al. "Preparation, Characterization and Immunogenicity of *Haemophilus influenzae* Type b Polysaccharide–Protein Conjugates," *J. Exp. Med.* 152:361–376 (1980).

Telford et al., "The *Pseudomonas aeruginosa* QuorumSensing Signal Molecule N–(3–oxododecanoyl)–L–Homoserine Lactone Has Immunomodulatory Activity," *Infect. Immun.* 66:36–42 (1998).

Wessels et al., "Immunogenicity in Animals of a Polysaccharide–Protein Conjugate Vaccine Against Type III Group B *Streptococcus*," *J. Clin. Invest.* 86:1428–1433 (1990).

*Primary Examiner*—S. Devi
(74) *Attorney, Agent, or Firm*—Nixon Peabody LLP

(57) ABSTRACT

The present invention relates to an immunogenic conjugate comprising a carrier molecule coupled to an autoinducer of a Gram negative bacteria. The immunogenic conjugate, when combined with a pharmaceutically acceptable carrier, forms a suitable vaccine for mammals to prevent infection by the Gram negative bacteria. The immunogenic conjugate is also used to raise and subsequently isolate antibodies or binding portions thereof which are capable of recognizing and binding to the autoinducer. The antibodies or binding portions thereof are utilized in a method of treating infections, a method of inhibiting autoinducer activity, and in diagnostic assays which detect the presence of autoinducers or autoinducer antagonists in fluid or tissue samples.

17 Claims, 3 Drawing Sheets

Figure 1:
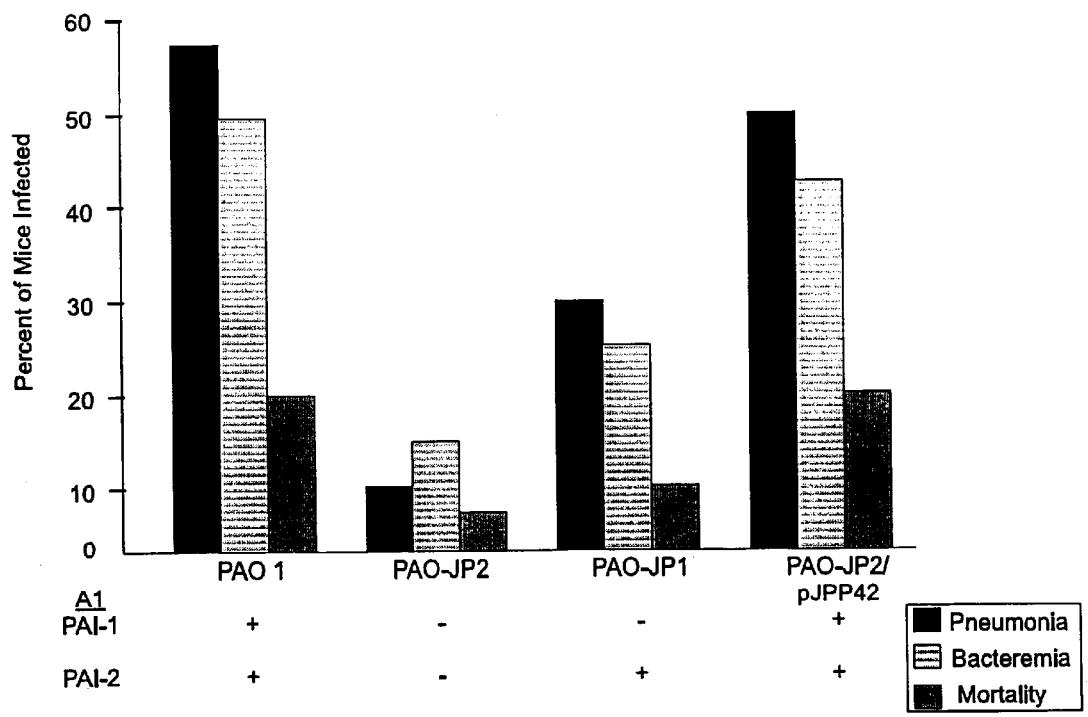

ANTIBODIES RAISED AGAINST IMMUNOGENIC CONJUGATES OF GRAM-NEGATIVE BACTERIAL AUTOINDUCER MOLECULES

This application is a divisional of U.S. patent application Ser. No. 09/293,687, filed Apr. 16, 1999, now U.S. Pat. No. 6,395,282, which claims priority to U.S. Provisional Patent Application Ser. No. 60/082,025, filed Apr. 16, 1998, which is incorporated herein in its entirety.

GOVERNMENT SUPPORT

This research was supported by grant number AI133713-04 from the National Institute of Health.

1. FIELD OF THE INVENTION

The present invention relates to an immunogenic conjugate comprising an autoinducer molecule of a Gram negative bacteria or a synthetic analogue thereof linked to a carrier molecule. The present invention also relates to antibodies and binding portions thereof capable of binding the immunogenic conjugate, and vaccines for the treatment or prevention of infection by autoinducer producing bacteria.

2. BACKGROUND OF THE INVENTION

Some pathogenic Gram negative bacteria produce chemical moieties known as bacterial autoinducers (BAIs). BAIs are produced by Gram negative bacteria as a mechanism for communicating with other bacteria when they have grown to a high cell density. This mechanism is known as quorum sensing.

BAIs assist in the transcriptional control of genes involved in a wide range of metabolic activities. When the bacterial population reaches a critical threshold, the concentration of BAIs also reach a concentration sufficient to enable the BAIs to bind a group of transcription factors, known as R-proteins. Binding of the BAIs to the R-proteins triggers binding of the newly formed BAI/R-protein complex to DNA, which then induces transcription of a group of genes. In the gram negative pathogenic bacteria, a subgroup of the activated genes are pathogenic determinants.

BAIs are small, non-imnmunogenic, lipid-soluble molecules which are capable of diffusing out of the bacteria, and into the environment where they enter host cells. BAIs share structural characteristics, in particular, they have a homoserine lactone ring with an N-acyl side chain. Variability between different BAIs resides primarily in the structure of the acyl side chain.

It has been proposed that in addition to regulating transcription in bacteria, the BAIs also regulate transcription in cells of an infected mammalian host. A list of presently known bacterial autoinducers (BAIs) and the Gram negative bacteria which produce them are identified in Table 1 below:

TABLE 1

| Gram negative bacteria: | Bacterial autoinducer (BAI): |
|---|---|
| Aeromonas hydrophila | AHAI |
| Agrobacterium tumefaciens | N-(3-oxo)-octanoyl-L-homoserine lactone (OOHL) |
| Burkholderia cepacia | N-octanoylhomoserine lactone |
| Chromobacterium violaceum | N-hexanoyl-L-homoserine lactone (HHL) |
| Enterobacter agglomerans | N-(3-oxo)-hexanoyl-L-homoserine lactone (OHHL) |
| Erwinia stewarti | OHHL |

TABLE 1-continued

| Gram negative bacteria: | Bacterial autoinducer (BAI): |
|---|---|
| Erwinia carotovora | OHHL |
| Escherichia coli | Structure not yet determined |
| Nitrosomas europea | OHHL |
| Photobacterium fischeri | OHHL, OOHL; OHL |
| Pseudomonas aeruginosa | N-(3-oxododecanoyl)-L-homoserine lactone (PAI-1); N-(butanoyl)-L-homoserine lactone (PAI-2) |
| Pseudomonas aureofaciens | Structure not yet determined |
| Rhizobium leguminosarum | N-(3-hydroxy)-tetradecanoyl-L-homoserine lactone (HtDeHL) |
| Serratia liquefaciens | PAI-2 |
| Vibrio fischeri | OHHL |
| Vibrio harveyi | N-(3-hydroxy)-butanoyl-L-homoserine lactone (HBHL) |
| Yersinia enterocolitica | OHHL, HHL |

The Gram negative bacterium *Pseudomonas aeruginosa* is an opportunistic human pathogen that causes infections in immunocompromised hosts. PAI-1 has been shown to inhibit the proliferation of lymphocytes in vivo and down-regulates expression of tumor necrosis factor and interleukin-12 (Telford et al., 1998, Infect Immun. 66(1) :36–42). *Pseudomonas aeruginosa* frequently colonizes the lungs of individuals with cystic fibrosis (Hoiby, N., 1974, Acta Pathologica Microbiolo. Scand. Sect. B. 82:551–558; Reynolds et al., 1975, Ann. Intern. Med. 82:819–832). This bacterium produces a number of extracellular virulence factors including exotoxin A, which is encoded by the toxA gene (Iglewski, B. H. and Kabat, D., 1975, Proc. Natl. Acad. Sci. USA. 72:2284–2288; Iglewski et al., 1978, Proc. Natl. Acad. Sci. USA. 75:3211–3215); an elastolytic protease encoded by the lasA gene; an elastolytic protease encoded by the lasB gene; and an alkaline protease encoded by the aprA gene (Morihara, K. and Homma, J. Y., 1985, Bacterial Enzymes and Virulence, ed. Holder, I. A. (CRC Press, Boca Raton, Fla.) pp. 41–79; Bever, R. A. and Iglewski, B. H., 1988, J. Bacteriol. 170:4309–4313; Kessler, E. and Saffrin, M., 1988, J. Bacteriol. 170:5241–5247).

*Pseudomonas aeruginosa* utilizes a partially redundant quorum sensing mechanism which includes two autoinducers, N-(3-oxododecanoyl)-L-homoserine lactone (PAI-1) and N-(butanoyl)-L-homoserine lactone (PAI-2) (see Table 1). These autoinducers control expression of a number of virulence factors, including the elastolytic proteases lasA and lasB, autoinducer synthase, alkaline protease, exotoxin A and rhamnolipid synthase. (Garnbello, et al., 1993, Infection & Immunity 61:1180–84; Latifi, et al., 1996, Mol. Microbiol. 21:1137–46; Passador, et al., 1993, Science 260:1127–30; Pesci, et al., 1997, J. Bact. 179:3127–32; Seed, et. al., 1995, J. Bact. 177:654–59; and Toder, et al., 1994, Infection & Immunity 62:1320–27.) It is the production of these virulence factors which enable *Pseudomonas aeruginosa* to invade and induce disease in humans.

Current treatments for Gram negative bacterial infections typically target surface antigens of the bacteria to make antibodies. Development of vaccines and diagnostic antibodies to autoinducers are hindered by the fact that autoinducers are not only non-immunogenic, but are also freely diffusible through the lipid bilayer and are not covalently attached to the bacteria. Several studies have demonstrated that a non-immunogenic bacterial capsular polysaccharide may be conjugated to an immunogenic compound to generate antibodies to the capsular polysaccharide (Anderson, U.S. Pat. No. 4,673,574 (conjugation of a fragment of a bacterial capsular polymer to a diphtheria or tetanus toxin or toxoid); Wessels et al., 1990, J. Clin. Invest. 86:1428–1433 (conjugation of a polysaccharide of type III group B Streptococcus to tetanus toxoid); and Schneerson et al., 1980, J. Exp. Med. 152:361–376 (conjugation of *H. influenzae* type b capsular polysaccharide to tetanus toxoid and other carriers.)) However, in contrast to autoinducers which are lipid diffusible, these anti-polysaccharide treatments are designed for production of antibodies specific to surface antigens covalently attached to the bacteria, resulting in lysis of the bacteria.

While synthetic autoinducer analogs limit bacterial growth in vitro, this approach fails to harness the capabilities of an active immune response that is a potentially long-lasting and effective therapeutic or prophylactic treatment (Pearson et al., U.S. Pat. No. 5,591,872). Furthermore, although autoinducer molecules themselves can be used in diagnostic bioassays, including bioluminescence, antibiotic production, or bacterial growth, these diagnostic assays fail to provide a prophylactic or therapeutic benefit to individuals exposed to autoinducer-producing Gram negative bacteria (Bycroft et al., U.S. Pat. No. 5,593,827).

3. SUMMARY OF THE INVENTION

The present invention relates to immunogenic conjugates comprising a carrier molecule covalently conjugated or otherwise bound to an autoinducer of a Gram negative bacteria of a compound of Formula (1):

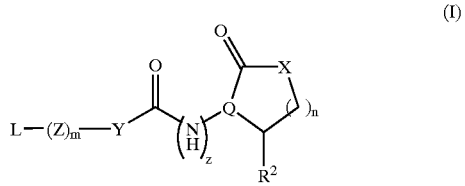

(I)

where X is O, S, N—($C_1$–$C_6$) alkyl, $NR^2$, N-phenyl; Y is $C_1$–$C_6$ straight or branched alkyl, $C_1$–$C_6$ straight or branched alkenyl, $C_1$–$C_6$ straight or branched alkynyl; Z is C=O, C=S, CHOH, C=N—$NR^1$, C=N—OH, $C_1$–$C_8$ straight or branched alkyl, $C_1$–$C_8$ straight or branched alkenyl, $C_1$–$C_8$ straight or branched alkynyl; L is $C_1$–$C_{18}$ straight or branched alkyl, $C_1$–$C_{18}$ straight or branched alkenyl, $C_1$–$C_{18}$ straight branched alkynyl, or —$CO_2H$, —$CO_2R^1$, —CHO, —C≡N, —N=C=O, —N=C=S, OH, $OR^1$, —CH=CH—$CH_2Br$, —CH=CH—$CH_2Cl$, —SAc or SH, where $R^1$ is $C_1$–$C_6$ straight or branched alkyl, m is 0 or 1; z is 0 or 1; $R^2$ is H, $C_1$–$C_6$ straight or branched alkyl, $C_1$–$C_6$ straight or branched alkenyl or $C_1$–$C_6$ straight or branched alkynyl, or $CO_2H$; and Q is CH or N; and n is 0–3 with the proviso that when n is 0, X is N—($C_1$–$C_6$ alkyl) or N-phenyl. In a specific embodiment, the carrier molecule comprises a lysine-containing protein, preferably, including but not limited to bovine serum albumin, chicken egg ovalbumin, keyhole limpet hemocyanin, tetanus toxoid, diphtheria toxoid, and thyroglobulin.

In specific embodiments, the autoinducer is produced by a Gram negative bacteria comprising *Aeromonas hydrophila, Agrobacterium tumefaciens, Burkholderia cepacia, Chromobacterium violaceum, Enterobacter agglomerans, Erwinia stewarti, Erwinia carotovora, Escherichia coli, Nitrosomas europea, Photobacterium fischeri, Pseudomonas aeruginosa, Pseudomonas aureofaciens, Rhizobium leguminosarum, Serratia liquefaciens,* or *Vibrio harveyi.*

In specific embodiments, the autoinducer comprises N-(3-oxododecanoyl)-L-homoserine lactone, N-(butanoyl)-L-homoserine lactone, N-hexanoyl-homoserine lactone, N-(3-oxohexanoyl)-homoserine lactone, N-β(hydroxybutyryl)-homoserine lactone, N-(3-oxooctanoyl)-L-homoserine lactone, or N-(3R-hydroxy-cis-tetradecanoyl)-L-homoserine lactone, preferably, N-(3-oxododecanoyl)-L-homoserine lactone (PAI-1) or N-(butanoyl)-L-homoserine lactone (PAI-2).

In a specific embodiment, the carrier molecule of the immunogenic conjugate has at least one amine group, the autoinducer has an N-acyl homoserine lactone structure, and the conjugate is the reductive amination product of the carrier molecule and the autoinducer.

The invention also relates to isolated antibodies or fragments thereof which specifically bind an autoinducer produced by a Gram negative bacteria. In an embodiment, the autoinducer is a compound of Formula (I) (described above). In another embodiment, the autoinducer comprises N-(3-oxododecanoyl)-L-homoserine lactone, N-(butanoyl)-L-homoserine lactone, N-hexanoyl-homoserine lactone, N-(3-oxohexanoyl)-homoserine lactone, N-β(hydroxybutyryl)-homoserine lactone, N-(3-oxooctanoyl)-L-homoserine lactone, or N-(3R-hydroxy-cis-tetradecanoyl)-L-homoserine lactone. In a specific embodiment, the autoinducer is N-(3-oxododecanoyl)-L-homoserine lactone or N-(butanoyl)-L-homoserine lactone.

The invention also relates to isolated antibodies or fragments thereof which specifically bind an autoinducer produced by a Gram negative bacteria in which the autoinducer is covalently conjugated or otherwise bound to a carrier molecule. The carrier molecule includes but is not limited to bovine serum albumin, chicken egg ovalbumin, keyhole limpet hemocyanin, tetanus toxoid, diphtheria toxoid, and thyroglobulin.

In specific embodiments, the autoinducer which is specifically bound by the antibodies or fragments thereof of the invention is produced by a Gram negative bacteria comprising *Aeromonas hydrophila, Agrobacterium tumefaciens, Burkholderia cepacia, Chromobacterium violaceum, Enterobacter agglomerans, Erwinia stewarti, Erwinia carotovora, Escherichia coli, Nitrosomas europea, Photobacterium fischeri, Pseudomonas aeruginosa, Pseudomonas aureofaciens, Rhizobium leguminosarum, Serratia liquefaciens,* or *Vibrio harveyi.*

The invention also relates to methods for detecting a Gram negative bacteria autoinducer in a sample comprising adding to the sample an antibody in which the antibody specifically binds the autoinducer of a Gram negative bacteria of a compound of Formula (I) (described above). In an embodiment, the autoinducer is produced by a Gram negative bacteria including but not limited to *Aeromonas hydrophila, Agrobacterium tuinetaciens, Burkholderia cepacia, Chromobacterium violaceum, Enterobacter agglomerans, Erwinia stewarti, Erwinia carotovora, Escherichia coli, Nitrosomas europea, Photobacterium fischeri, Pseudomonas aeruginosa, Pseudomonas aureofaciens, Rhizobium leguminosarum, Serratia liquefaciens,* or *Vibrio harveyi.*

The invention also relates to methods of treating or preventing an infectious disease in a subject comprising administering an amount of an immunogenic conjugate in which the immunogenic conjugate comprises a carrier molecule covalently conjugated or otherwise bound to an autoinducer of a Gram negative bacteria of a compound of Formula (I) (described above); preferably, the subject is a human.

The invention also relates to methods of treating or preventing an infectious disease in a subject comprising administering an amount of an antibody or fragment thereof which specifically binds an autoinducer of a Gram negative bacteria of a compound of Formula (I) (described above); preferably, the subject is a human.

The invention also relates to diagnostic kits and pharmaceutical compositions comprising the immunogenic conjugates or antibodies or fragments thereof of the invention.

The present invention also relates to methods of inhibiting autoinducer activity. The methods comprise contacting an effective amount of the antibody or binding portion thereof with an autoinducer under conditions effective to bind the autoinducer in which the amount is effective to treat or prevent infection by Gram negative bacteria.

4. BRIEF DESCRIPTION OF THE DRAWINGS

FIG. 1. Comparison of the role of autoinducers PAI-1 and PAI-2 in the virulence of *Pseudomonas aeruginosa*. Neonatal mice were infected with *Pseudomonas aeruginosa* strains PAO1(wild type), PAO-JP2 (bearing the lasI/rhII double deletion), PAO-JP1 (bearing lasI single deletion), and PAO-JP2/pJPP42 (bearing the lasI/rhII double deletion with plasmid expressing lasI/rhII). The mice were sacrificed and examined for pneumonia (black bars), bacteremia (light gray bars), and mortality (dark gray bars).

Figure 2:
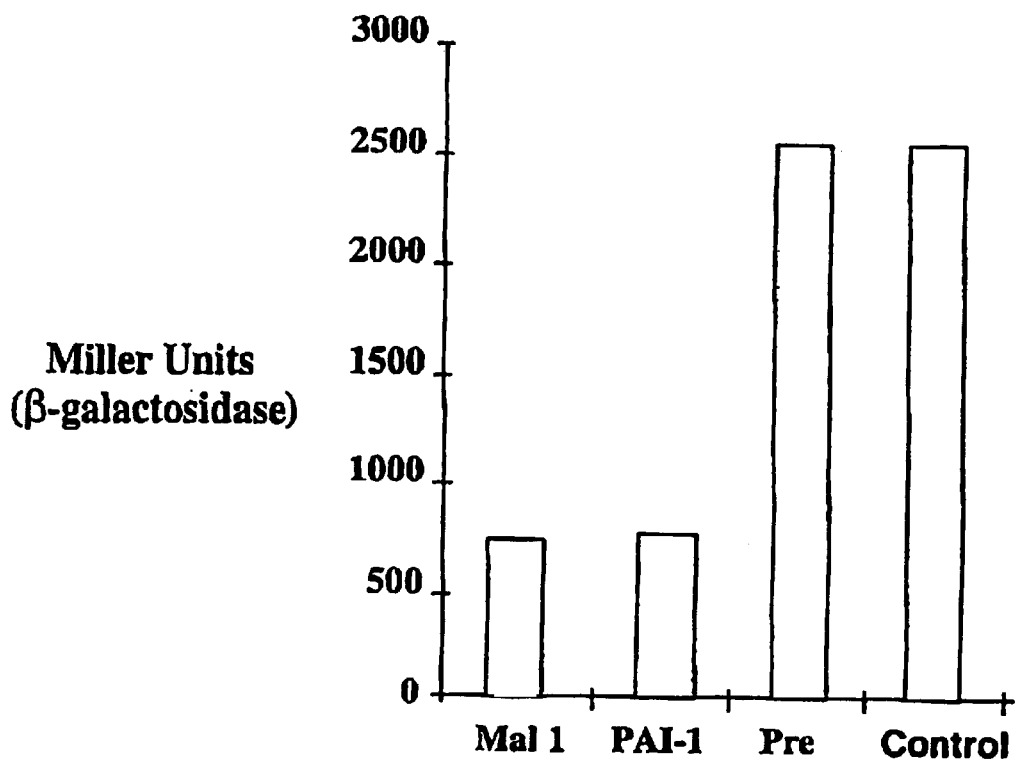

FIG. 2. The effect of anti-PAI-1 murine polyclonal antibodies on an *E. coli* transcriptional bioassay. A 1:10 dilution of mouse serum was preincubated with 100 pM PAI-1 prior to addition to the bioassay. "Mal 1" is compound D conjugate immune serum, "PAI-1" is PAI-1 conjugate immune serum, "Pre" is serum from mice prior to any immunization and "control" is PAI-1 without addition of serum. Addition of immune serum exhibited a 70% inhibition in the production of β-galactosidase.

Figure 3:
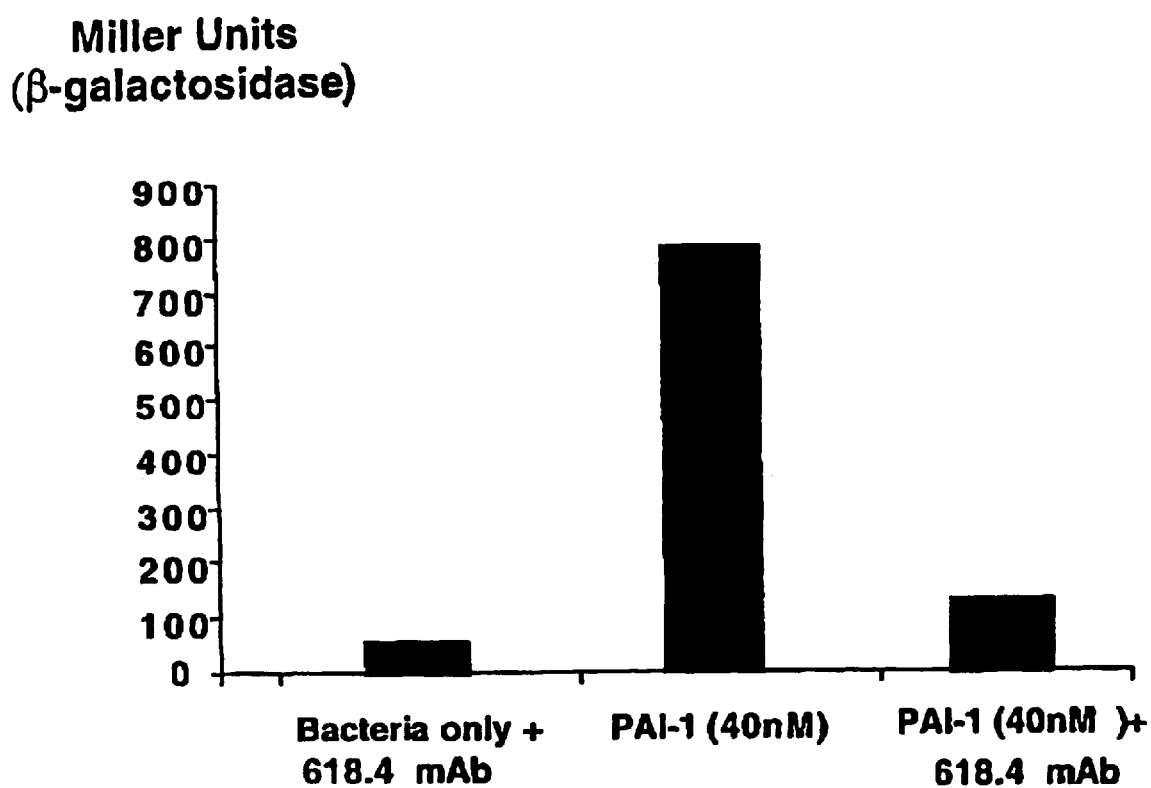

FIG. 3. The effect of anti-PAI-1 monoclonal antibodies in a *Pseudomonas aeruginosa* transcriptional bioassay. When an anti-PAI-1 monoclonal antibody (618.4) was added to 40 nM PAI-1 prior to addition to the bioassay an 80% inhibition in β-galactosidase production was exhibited.

5. DETAILED DESCRIPTION OF THE INVENTION

The present invention provides for the production of immunogenic conjugates of autoinducers and immunogenic conjugates for use as vaccines or for production of antibodies useful for immunotherapy or diagnostic assays.

Solely for ease of explanation, the description of the invention is divided into the following sections: (A) isolation of homoserine lactones; (B) conjugation of autoinducers to immunogenic carriers; (C) generation of antibodies to BAI immunogenic conjugates; (D) therapeutic uses of immunogenic conjugates or antibodies thereto; (E) diagnostic assays.

5.1 Isolation and Synthesis of Homoserine Lactones

Autoinducers of Gram negative bacteria can be isolated and purified by various methods known in the art. Purification of homoserine lactones through chemical methods can be used to isolate naturally produced autoinducers. The autoinducer N-(β-ketocaproyl) homoserine lactone has been purified from a culture supernatant of *Erwinia carotovora* (Bycroft et al., U.S. Pat. No. 5,593,827, hereby incorporated by reference). Following bacterial culture centrifugation, the autoinducer is extracted from the supernatant using ethyl acetate, the resulting sample is mixed with water and the ethyl acetate removed. Next, the sample is passed through a column containing a hydrophobic resin which is eluted with a methanol in water solution to remove the autoinducer. The methanol in water solution, now containing the autoinducer, is concentrated by rotary evaporation. Thereafter, the autoinducer is purified using HPLC and additional rotary evaporation.

A similar process has been developed for purifying the naturally occurring autoinducer of *Pseudomonas aeruginosa*, N-(3-oxododecanoyl)-L-homoserine lactone (PAI-1) (Pearson et al., U.S. Pat. No. 5,591,872, which is hereby incorporated by reference). First, cells and culture fluid are separated by centrifugation and the culture fluid subsequently passed through a 0.2 μm pore-size filter. The filtered material is repeatedly extracted using alternating ethanol/ethyl acetate steps. The sample is subsequently dissolved in methanol and purified using HPLC with reverse phase column. Additional extraction and purification by HPLC yield the isolated autoinducer PAI-1.

Eberhard et al., 1981, Biochem. 20:2444–49, which is hereby incorporated by reference, describes a process for chemically synthesizing N-(3-oxohexanoyl)-homoserine lactone. U.S. Pat. No. 5,591,872 to Pearson et al., establishes that the process of Eberhard et al. may also be used to synthesize N-(3-oxododecanoyl)-L-homoserine lactone (PAI-1), by using a different starting material (i.e., ethyl 3-oxododecanoate rather than ethyl 3-oxohexanoate). Therefore, it may be appreciated by one of ordinary skill in the art that the procedure of Eberhard et al. may be used to synthesize a variety of autoinducer molecules and their derivatives by utilizing different starting materials.

Compounds of the Formula (I) where L is $CO_2H$ or $CO_2$-alkyl, m is 0, Y is $CH_2$, n is 1, Q is CH, and X is O may be prepared according to Scheme I. Reaction of L-homoserine lactone hydrochloride (B) with malonic acid mono tert-butylester (A) in methylene chloride at room temperature in the presence of an organic base, such as triethylamine, and a coupling agent, such as benzotriazol-1-yloxytris (dimethylamino) phosphonium hexafluorophosphate yielded the corresponding amide (C). Amide (C) was deprotected under acidic conditions using trifluoroacetic acid (TFA) in methylene chloride at room temperature to yield the carboxylic acid (D). Homoserine derivatives of the formula (D) can be conjugated to amine or alcohol functionalities on the appropriate carrier protein by reaction with the carboxylic acid moiety under standard conditions to one skilled in the art to form an amide or ester conjugate, respectively, with the carrier protein.

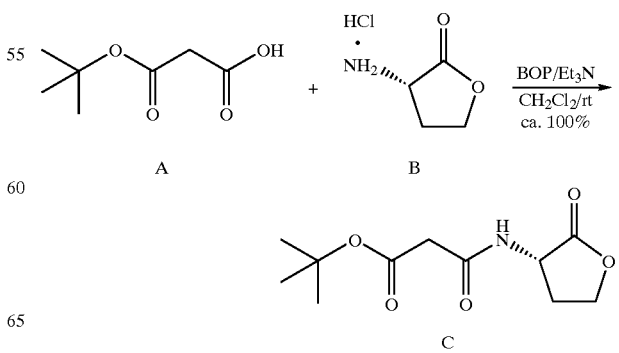

Scheme I

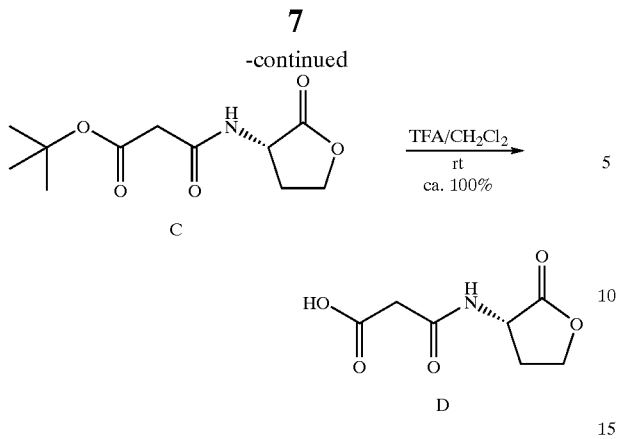

Compounds of the Formula (I) where Y and L are alkyl, Q is CH, n is 1 and m is 0 were prepared in a single step as outlined in Scheme 2. Thus, reaction of the sodium or lithium salts of the fatty acids 1–3 with optically pure L-homoserine lactone hydrochloride (Sigma Chemical Co., St. Louis, Mo.) in the presence of the commercially available water soluble coupling agent 1-(3-dimethylaminopropyl)-3-ethylcarbodiimide hydrochloride (Aldrich Chemical Company, Milwaukee, Wis.), provided the waxy amides 5–7 in good yield. In each case, the crude products were conveniently purified by recrystallization from ethyl acetate/hexane.

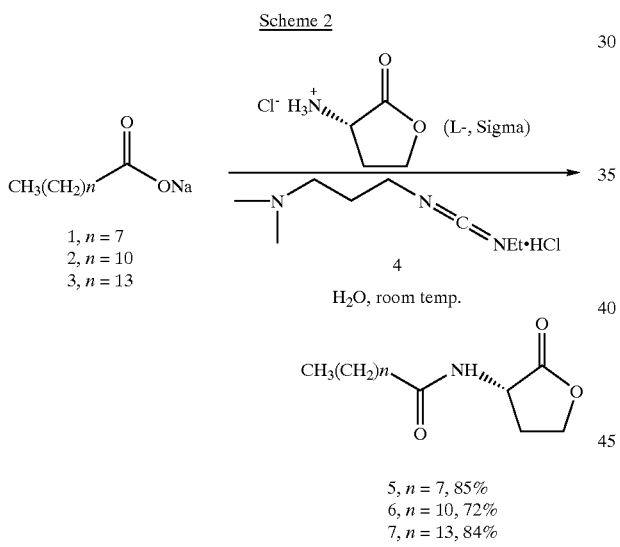

The natural form of Pseudomonas autoinducer (PAI) 13 was synthesized in a novel six step sequence as outlined in Scheme 3. Standard acylation of Meldrums acid with decanoyl chloride in the presence of pyridine provided the acyl Meldrums species 8. Reaction of 8 with methanol under reflux conditions then provided the beta-ketoester 9 in good yield. The C3 carbonyl group of 9 was then protected as its ketal under standard conditions and hydrolysis of the methyl ester functionality under basic conditions then afforded the carboxylate 10. Coupling of 10 and L-homoserine lactone hydrochloride under aqueous conditions in the presence of water soluble carbodiimide 4 then provided the amide 11 in good yield. Final deprotection of 11 was accomplished with dilute acid affording the target keto-amide 13 (PAI). An analogous sequence was carried out in order to prepare the keto-amide 14 bearing a thiolactone moiety. In this sequence, optically pure L-homocysteine thiolactone hydrochloride (available from Sigma) was substituted for L-homoserine lactone hydrochloride in the carbodiimide mediated coupling step. The resulting dioxolane-amide 12 was then deprotected with dilute acid to provide the keto-amide 14.

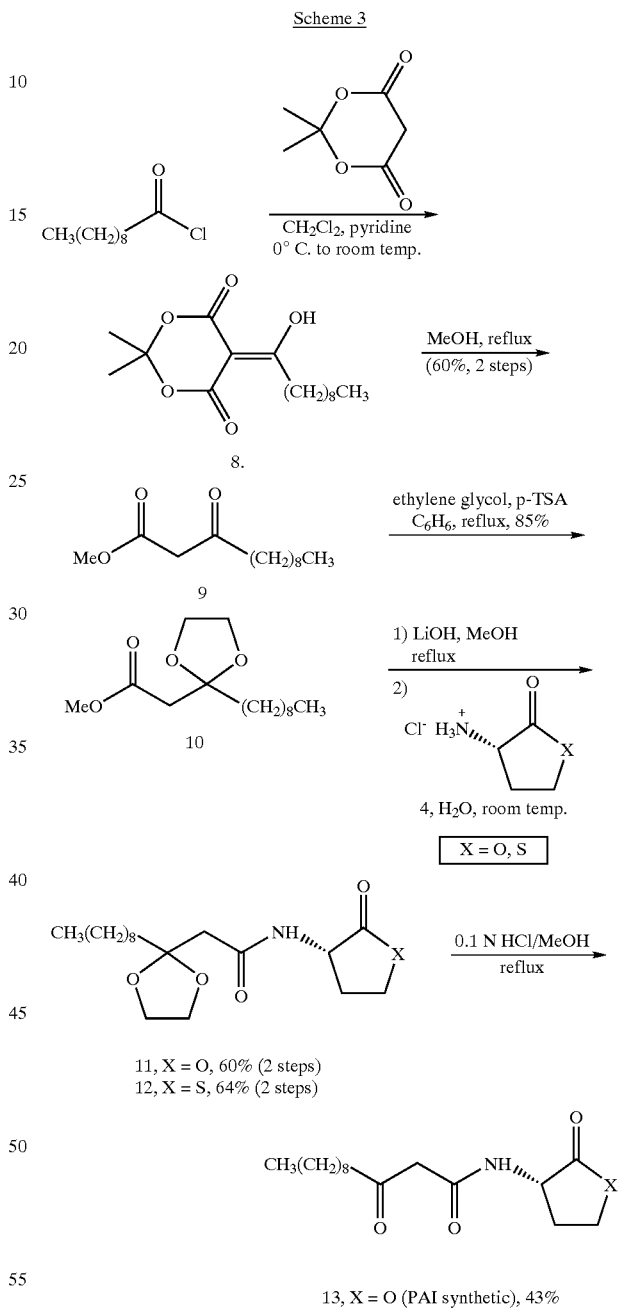

Compounds of the Formula (I) where Z is CHOH, Y is CH$_2$, L is alkyl, n is 1, Q is CH and X is O were prepared by reduction of the C3 keto group of 13 as outlined in Scheme 4. Thus, low temperature reduction of 13 with sodium borohydride in methanol provided a diastereomeric mixture of alcohols 15.

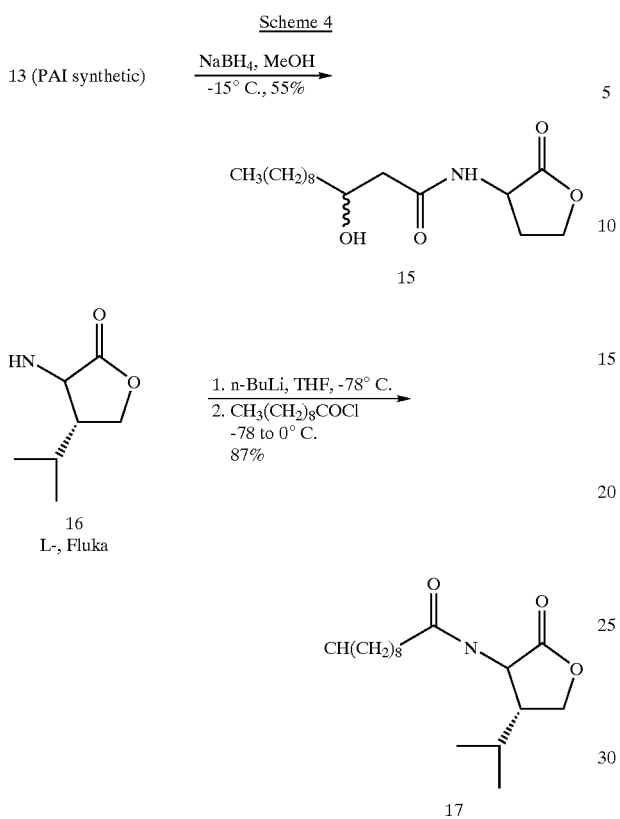

Compounds of the Formula (I) where X is O Q is N, m is 0, z is 0, and $R^2$ is straight or branched alkyl were prepared by direct acylation of 16 with decanoyl chloride (Scheme 4). Deprotonation of commercially available optically pure 16 with BuLi followed by quenching the resulting anion with decanoyl chloride, provided the acylated oxazolidinone 17 in good yield.

Compounds of the Formula (I) where X is O Y is $CH_2$, Z is C=O, Q is CH, n is 1, and L is $C_1$–$C_{18}$ straight or branched alkenyl may be prepared by the method of Scheme 5. Careful oxidation of commercially available trans-4-decanal with sodium hypochlorite in the presence of sulfamic acid (as chlorine scavenger), provided crude acid 18 which was not purified, but converted directly to the acid chloride 19 with oxalyl chloride and DMF(cat.). Reaction of 19 with Meldrums acid in the presence of pyridine provided the acyl Meldrums species 20. Heating crude 20 in methanol then afforded the beta-ketoester 21 which was then purified by flash chromatography. Protection of the ketone carbonyl group of 21 as its ketal followed by hydrolysis of the ester with lithium hydroxide gave the carboxylate salt 23. Coupling of 23 and L-Homoserine lactone hydrochloride in the presence of the carbodiimide 4 in aqueous medium, provided the amide 24. Finally, deprotection of 24 under acidic conditions gave the unsaturated keto-amide 25 in 36% yield over 3 steps.

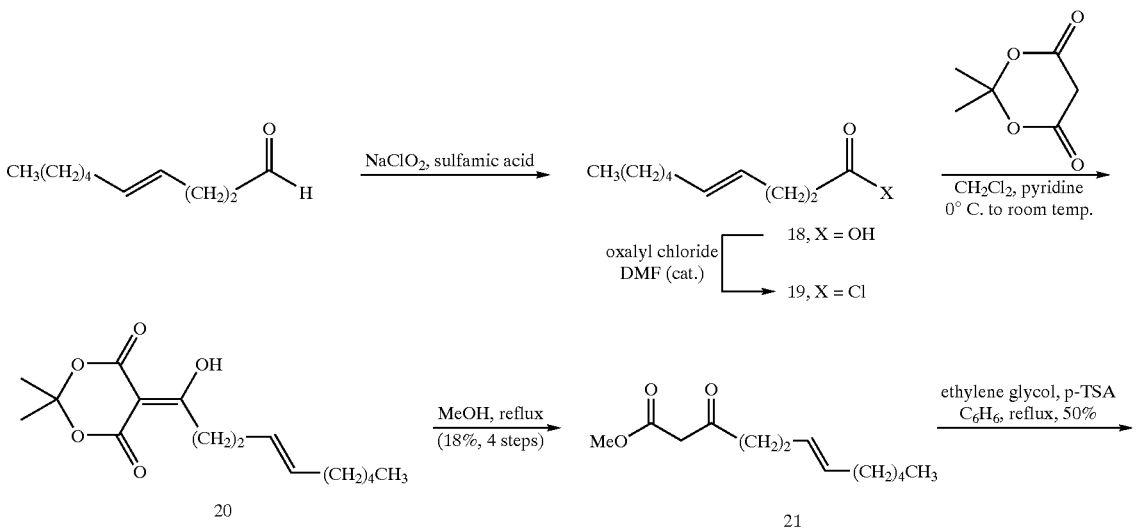

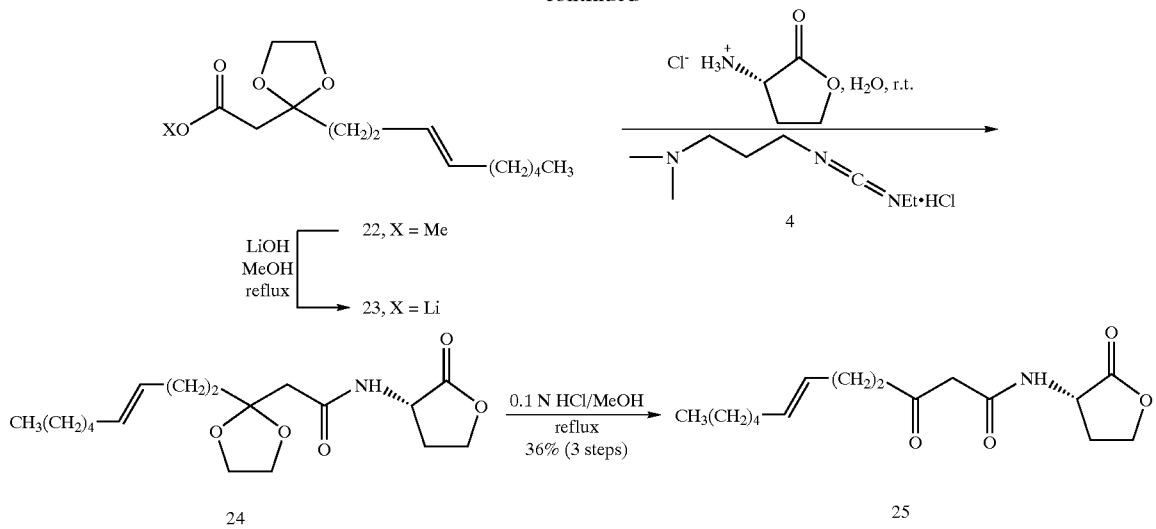

Compounds of the Formula (I) where X is NH, Q is CH, Y is CH$_2$, Z is C=O, L is alkyl, n is 1, m is 1, and Z is C=O were prepared according to Scheme 6. The keto-lactam 28 was prepared as outlined in Scheme 6. Hydrolysis of 10 with lithium hydroxide followed by carbodiimide mediated coupling with aminolactam hydrochloride 26 provided the protected lactam 27. The aminolactam hydrochloride 26 was prepared from commercially available (S)-(+)-2,4-Diaminobutyric acid hydrochloride (Aldrich Chemical Co.) according to the literature procedure. D. W. Adamson, *J. Chem. Soc.* 1943:39–41. Hydrolysis of 27 with dilute acid then gave the target keto-lactam 28 in good overall yield.

Scheme 6

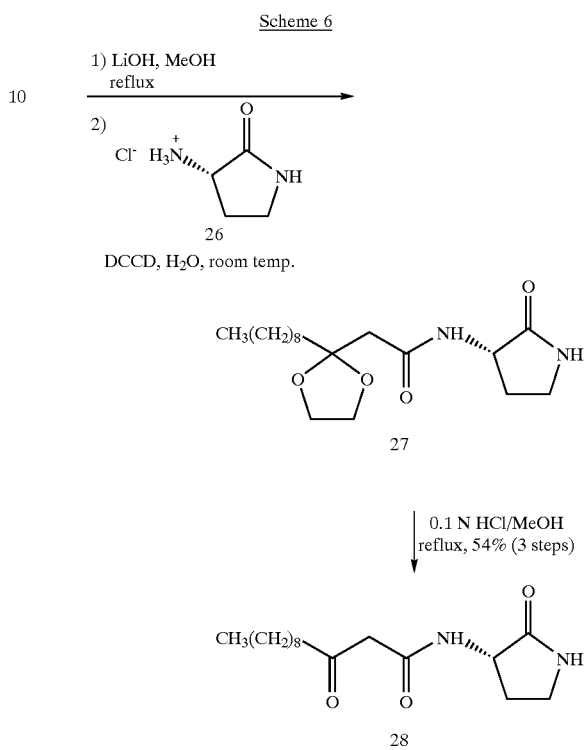

Compounds of the Formula (I) where Y is C$_1$–C$_6$ alkenyl, m is 0, and Z is CO$_2$H can be made by the reaction of homoserine lactone with maleic anhydride in methylene chloride at room temperature to yield compound 29. (Scheme 7). Linshitz, Y., et al., *J. Amer. Chem. Soc.*, 77, 1265–6 (1955).

Scheme 7

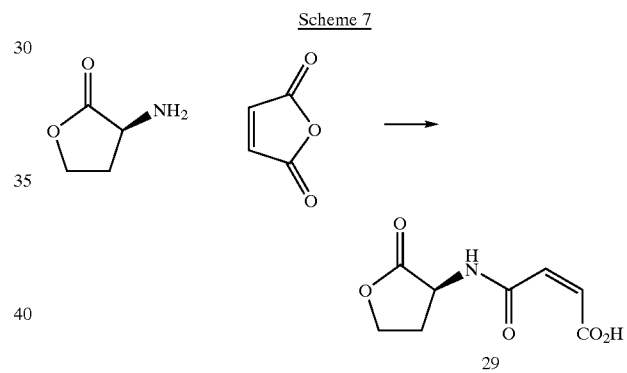

The carboxylic acid moiety can then be coupled to a carrier protein containing a free amino or hydroxy group under standard conditions to yield the corresponding immunogenic conjugate.

Autoinducer molecules suitable for use in forming immunogenic conjugates of the present invention are the autoinducers of Gram negative bacteria of a compound of Formula (I) and derivatives thereof. In particular, the autoinducers used to form the immunogenic conjugate of the present invention are the autoinducers of the following Gram negative bacteria: *Aeromonas hydrophiia, Agrobacterium tumefaciens, Burkholderia cepacia, Chromobacterium violaceum, Enterobacter agglomerans, Erwinia stewarti, Erwinia carotovora, Escherichia coli, Nitrosomas europea, Photobacterium fischeri, Pseudomonas aeruginosa, Pseudomonas aureofaciens, Rhizobium leguminosarum, Serratia liqueffaciens*, and *Vibrio harveyi*.

Preferred autoinducer molecules are N-(3-oxododecanoyl)-L-homoserine lactone, N-(butyryl)-L-homoserine lactone, N-butanoyl-L-homoserine lactone, N-hexanoyl-homoserine lactone, N-(3-oxohexanoyl)-homoserine lactone, N-β-(hydroxybutyryl)-homoserine lactone, N-(3-oxooctanoyl)-L-homoserine lactone, N-(3R-hydroxy-cis-tetradecanoyl)-L-homoserine lactone, other N-acyl homoserine lactones, their derivatives and analogs.

The structures of various exemplary autoinducer molecules are shown below:

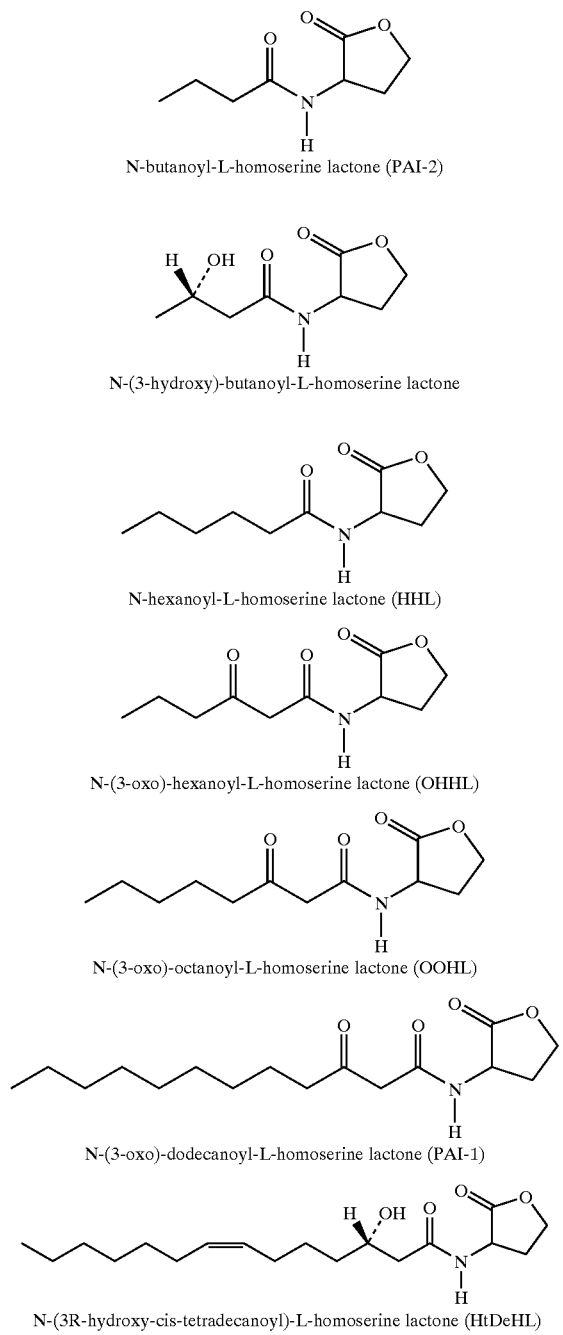

N-butanoyl-L-homoserine lactone (PAI-2)

N-(3-hydroxy)-butanoyl-L-homoserine lactone

N-hexanoyl-L-homoserine lactone (HHL)

N-(3-oxo)-hexanoyl-L-homoserine lactone (OHHL)

N-(3-oxo)-octanoyl-L-homoserine lactone (OOHL)

N-(3-oxo)-dodecanoyl-L-homoserine lactone (PAI-1)

N-(3R-hydroxy-cis-tetradecanoyl)-L-homoserine lactone (HtDeHL)

5.2 Bacterial Autoinducer Conjugation to a Carrier

Once the desired autoinducer is isolated, the immunogenic conjugates of the present invention are formed by coupling the carrier molecule to the autoinducer. Typically, these reactions are conducted by reacting available hydroxy or amino groups in a protein, with a compound of the formula (I) as shown below:

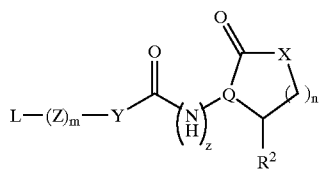

(I)

where X is O, S, N—($C_1$–$C_6$) alkyl, $NR^2$, N-phenyl; Y is $C_1$–$C_6$ straight or branched alkyl, $C_1$–$C_6$ straight or branched alkenyl, $C_1$–$C_6$ straight or branched alkynyl; Z is C=O, C=S, CHOH, C=N—$NR^1$, C=N—OH, $C_1$–$C_8$ straight or branched alkyl, $C_1$–$C_8$ straight or branched alkenyl, $C_1$–$C_8$ straight or branched alkynyl; L is $C_1$–$C_{18}$ straight or branched alkyl, $C_1$–$C_{18}$ straight or branched alkenyl, $C_1$–$C_{18}$ straight branched alkynyl, or —$CO_2$H, —$CO_2R^1$, —CHO, —C≡N, —N=C=O, —N=C=S, OH, $OR^1$, —CH=CH—$CH_2$Br, —CH=CH—$CH_2$Cl, —SAc or SH, where $R^1$ is $C_1$–$C_6$ straight or branched alkyl, m is 0 or 1; z is 0 or 1; $R^2$ is H, $C_1$–$C_6$ straight or branched alkyl, $C_1$–$C_6$ straight or branched alkenyl or $C_1$–$C_6$ straight or branched alkynyl, or $CO_2$H; and Q is CH, or N; and n is 0–3 with the proviso that when n is 0, X is N—($C_1$–$C_6$ alkyl) or N-phenyl.

The reactions are performed under acidic or basic conditions in the presence of a suitable coupling agent. For example, an autoinducer of Gram negative bacteria may contain a reactive ketone moiety in a compound of Formula (I). The reaction of the reactive ketone moiety of a compound of Formula (I) with a carrier molecule such as a protein containing a free amino group will produce a Schiff base which can then be reduced with sodium cyanoborohydride to produce the corresponding amine (reductive amination). Sodium cyanoborohydride is the preferred agent for the reduction of Schiff bases in the presence of other ketone moieties present in the autoinducer compound of Formula (I).

Other reducing agents can be used to reductively aminate ketone moieties instead of sodium cyanoborohydride. Their suitability will depend upon the functionalities present in the autoinducer compound of Formula (I). The alternative reducing agents include hydrogen and a catalyst of either sodium triacetoxyborohydride (Carson et al., 1990, Tetrahedron Letters, 31, 5595), sodium borohydride (Schellenberg, 1963, J. Org. Chem., 28, 3259) alcoholic potassium hydroxide (Watanabe et al.,, 1974, Tetrahedron Letters, 1879) or $BH_3$-Pyridine (Pelter et al., 1984, J. Chem. Suc. Perkin Trans. 1:717). The reductive amination process is carried out using the method set forth by Schwartz and Gray, "Proteins Containing Reductively Aminated Disaccharides: Synthesis and Chemical Characterization," *Arch. Biochem. Biophys.* 181:542–549 (1977), which is hereby incorporated by reference.

Alternatively, a carrier molecule such as a protein containing a free amino group can be coupled to carbon—carbon multiple bonds present in a compound of Formula (I) under basic conditions to form an amine conjugate or imine conjugate in the case where addition occurs to an alkyne. The free amino group of a protein could also add to an isocyanate or isothiocyanate moiety of a compound of Formula (I) to yield a urea or thiourea conjugate, respectively. Vishnyakora, et al., *Russ. Chem. Rev.* 54, 249–261 (1985). Additionally, amine conjugate containing a compound of Formula (I) can be made by reaction of an allylic halide moiety with a protein containing a free amino group under basic conditions.

For example, the *Pseudomonas aeruginosa* autoinducer PAI-1 may be conjugated to a carrier molecule such as a lysine containing protein (i.e., bovine serum albumin). PAI-1 and the protein carrier molecule are mixed at a 1:10 molar ratio in phosphate buffer (pH 7.0). PAI-1, via the keto group, interacts with the terminal amino groups of lysines on the surface of the protein carrier molecule to form a Schiff base. The mixture is incubated until conjugation is substantially complete. After conjugation, the intermediate Schiff base formed between PAI-1 and the protein carrier molecule is reduced with sodium cyanoborohydride. Finally, the mixture is dialyzed for removal of unbound PAI-1 and residual cyanoborohydride.

Alternatively, a BAI may be prepared by coupling a carboxylic acid moiety of L or $R^2$ of a compound of Formula (I) with an amine of a protein to form a peptide conjugate. As coupling reagents, one can use any standard peptide coupling activation method for carboxylic acid moieties such as those exemplified in schemes 1–6 described earlier, or other coupling agents or methods (e.g., photocoupling) known to those skilled in the art.

As another alternative, the BAI may be non-covalently bound to the carrier molecule by being absorbed to the carrier molecule using techniques commonly known in the art.

Suitable carrier molecules are those which are safe for administration to mammals and immunologically effective as carriers. Safety would include the absence of primary toxicity and minimal risk of allergic complications. Preferred carrier molecules are bovine serum albumin, chicken egg ovalbumin, keyhole limpet hemocyanin, tetanus toxoid, diphtheria toxoid, thyroglobulin, and other lysine containing proteins. Each of the preferred carrier molecules fulfill these criteria, because they are non-toxic and the incidence of allergic reaction is well known.

The formation of immunogenic conjugates comprising an autoinducer of a Gram negative bacteria and a carrier molecule enables a wide array of therapeutic and/or prophylactic agents and diagnostic procedures for, respectively, treating or preventing infection by Gram negative bacteria and detecting the presence of autoinducer molecules produced thereby.

5.3 Generation of Antibodies to BAI Immunogenic Conjugates

Another aspect of the present invention relates to isolated antibodies or binding portions thereof which specifically bind an autoinducer of the present invention. The present invention also encompasses pharmaceutical compositions comprising the antibodies or binding portions thereof and a pharmaceutically acceptable carrier.

An autoinducer immunogenic conjugate or autoinducer or derivative thereof, may be used as an immunogen to generate antibodies which recognize the said immunogen. The antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies or binding portions thereof, or compositions containing the same, are useful in treating mammals, preferably humans, exposed to or otherwise infected with a autoinducer producing Gram negative bacteria. Methods of treatment using the compositions of the present invention include but are not limited to passive immunotherapy, idiotype vaccination, etc. Methods of treatment encompassed by the present invention comprise administration of a therapeutically effective amount of the antibody or binding portion thereof in which the antibody or binding portion thereof is capable of binding an autoinducer of a Gram negative bacteria.

Various procedures known in the art may be used for the production of polyclonal antibodies to an autoinducer immunogenic conjugate. For the production of antibodies, various host animals can be immunized by injection with an immunogenic conjugate, or a synthetic version, or derivative (e.g., fragment) thereof. Such host animals include but are not limited to rabbits, mice, rats, etc. Adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Various procedures for raising polyclonal antibodies are described in E. Harlow, et al., editors, *Antibodies: A Laboratory Manual* (1988), which is hereby incorporated by reference. For an illustrative example, see section 6.2, infra.

For preparation of monoclonal antibodies directed toward an autoinducer or analog thereof, any technique which provides for the production of antibody molecules by continuous cell lines in culture may be used. For example, the hybridoma technique of Kohler and Milstein (1975, Nature 256:495–497), the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96). Human antibodies may be used and can be obtained by using human hybridomas (Cote et al., 1983, Proc. Natl. Acad. Sci. USA 80:2026–2030) or by transforming human B cells with EBV virus in vitro (Cole et al., 1985, in Monoclonal Antibodies and Cancer Therapy, Alan R. Liss, pp. 77–96). In addition, monoclonal antibodies can be produced in germ-free animals utilizing recent technology (PCT/US90/02545).

In addition, techniques developed for the production of "chimeric antibodies" (Morrison, et al., 1984, Proc. Natl. Acad. Sci., 81,6851–6855; Neuberger, et al., 1984, Nature 312,604–608; Takeda, et al., 1985, Nature, 314,452–454, incorporated herein by reference in their entirety) by splicing the genes from a mouse antibody molecule of appropriate antigen specificity together with genes from a human antibody molecule of appropriate biological activity can be used, for example, the genes from a mouse antibody molecule specific for an autoinducer can be spliced together with genes from a human antibody molecule of appropriate biological activity. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.)

In addition, techniques have been developed for the production of humanized antibodies. (See, e.g., Queen, U.S. Pat. No. 5,585,089 and Winter, U.S. Pat. No. 5,225,539, which are incorporated herein by reference in their entirety.) An immunoglobulin light or heavy chain variable region consists of a "framework" region interrupted by three hypervariable regions, referred to as complementarity determining regions (CDRs). The extent of the framework region and CDRs have been precisely defined (see, "Sequences of Proteins of Immunological Interest", Kabat, E. et al., U.S. Department of Health and Human Services (1983), incorporated hereinby reference in their entirety). Briefly, humanized antibodies are antibody molecules from non-human species having one or more CDRs from the non-human species and a framework region from a human immunoglobulin molecule.

Alternatively, techniques described for the production of single chain antibodies (U.S. Pat. No. 4,946,778; Bird, 1988, Science 242, 423–426; Huston, et al., 1988, Proc. Natl. Acad. Sci. USA 85, 5879–5883; and Ward, et al., 1989, Nature 334, 544–546, incorporated herein by reference in their entirety) can be adapted to produce single chain antibodies against an immunogenic conjugate of the present invention. Single chain antibodies are formed by linking the heavy and light chain fragments of the Fv region via an amino acid bridge, resulting in a single chain polypeptide.

In another embodiment, the methods of the present invention encompass use of antibody fragments comprising the idiotype of the whole antibody. Such fragments include but are not limited to: the F(ab')$_2$ fragments, which can be produced by pepsin digestion of the antibody molecule and the Fab fragments, which can be generated by reducing the disulfide bridges of the F(ab')$_2$ fragments (J. Goding, *Monoclonal Antibodies: Principles and Practice*, pp. 98–118 (N.Y. Academic Press 1983), which is incorporated herein by reference). Alternatively, the Fab fragments can be generated by treating the antibody molecule with papain and a reducing agent. Alternatively, Fab expression libraries may be constructed (Huse, et al., 1989, Science, 246:1275–1281, incorporated herein by reference in its entirety) to allow rapid and easy identification of monoclonal Fab fragments with the desired specificity.

In an embodiment of the invention, molecules comprising the binding portion of antibodies which specifically bind an autoinducer or the epitope of an autoinducer may be used in the methods of the invention. Such molecules include peptides, derivatives and analogs thereof, and peptide mimetics.

The autoinducer specific antibodies may be isolated by standard techniques known in the art such as immunoaffinity chromatography, centrifugation, precipitation, etc. Screening for the desired antibody can be accomplished by techniques known in the art including but not limited to, competitive and non-competitive assay systems using techniques such as radioimmunoassays, ELISA (enzyme linked immunosorbent assay), "sandwich" immunoassays, immunoradiometric assays, gel diffusion precipitin reactions, immonodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled.

The foregoing antibodies can be used for treating or preventing diseases caused by the autoinducer producing Gram negative bacteria or for detecting and measuring the activity of the autoinducer of the invention, e.g., for imaging these autoinducers, measuring levels thereof in appropriate physiological samples, in diagnostic assays, etc. as discussed in section 5.5 infra.

The antibodies generated by the vaccine formulations of the present invention can also be used in the production of antiidiotypic antibody. The antiidiotypic antibody can then in turn be used for immunization, in order to produce a subpopulation of antibodies that bind the initial antigen of the pathogenic microorganism (Jerne, 1974, Ann. Immunol. (Paris) 125c:373; Jerne, et al., 1982, EMBO J. 1:234).

5.4 Therapeutic Uses of Immunogenic Conjugates or Antibodies Thereto

Autoinducer immunogenic conjugates and antibodies which specifically bind an autoinducer by a Gram negative bacteria can be used for treating or preventing an infectious disease caused by a Gram negative bacteria.

5.4.1 Administration and Formulation

Immunogenic conjugates comprising an autoinducer of a Gram negative bacteria of a compound of Formula (I) coupled to a carrier molecule can be used as vaccines for immunization against said autoinducer producing Gram negative bacteria. The vaccines, comprising the immunogenic conjugate in a pharmaceutically acceptable carrier, are useful in a method of immunizing mammals, preferably humans, for treatment or prevention of infections by the said autoinducer producing Gram negative bacteria.

The antibodies generated against the autoinducer immunogenic conjugate of the present invention by immunization with the autoinducer immunogenic conjugate can be used in passive immunotherapy and generation of antiidiotypic antibodies for treating or preventing infectious disease caused by a Gram negative bacteria.

In a specific embodiment, an immunogenic conjugate comprising the *Pseudomonas aeruginosa* autoinducer PAI-1 (see Table 1) is administered as a vaccine to *Pseudomonas aeruginosa*. In another embodiment, an immunogenic conjugate comprising the *Pseudomonas aeruginosa* autoinducer PAI-2 (see Table 1) is administered as a vaccine. In another embodiment, an immunogenic conjugate comprising PAI-1 is administered before, during, or after administration of an immunogenic conjugate comprising PAI-2. In another embodiment, an autoinducer immunogenic conjugate vaccine is administered before, during or after administration of an effective amount of an antibody or binding portion thereof which has been raised against an immunogenic conjugate of the type described above.

In an embodiment, an antibody or binding portion thereof which specifically binds an immunogenic conjugate comprising PAI-1 is administered. In another embodiment, an antibody or binding portion thereof which specifically binds PAI-2 is administered. In another embodiment the antibody which specifically binds PAI-1 is administered before, during or after administration of an antibody which specifically binds PAI-2.

Methods of administration of the compositions of the invention (i.e., BAI immunogenic conjugate vaccine or antibodies specific to the BAI immunogenic conjugates) include but are not limited to oral, intradermal, intramuscular, intraperitoneal, intravenous, subcutaneous, intranasal routes, and scarification (scratching through the top layers of skin, e.g., using a bifurcated needle).

The patient to which the composition is administered is preferably a mammal, including but not limited to cows, horses, sheep, pigs, fowl (e.g. chickens), goats, cats, dogs, hamsters, mice and rats. In a preferred embodiment the subject is a human.

The formulations of the invention comprise an effective immunizing amount of one or more autoinducer immunogenic conjugate or antibody thereto and a pharmaceutically acceptable carrier or excipient. Subunit vaccines comprise an effective immunizing amount of one or more Antigens and a pharmaceutically acceptable carrier or excipient. Pharmaceutically acceptable carriers are well known in the art and include but are not limited to saline, buffered saline, dextrose, water, glycerol, sterile isotonic aqueous buffer, and combinations thereof. One example of such an acceptable carrier is a physiologically balanced culture medium containing one or more stabilizing agents such as stabilized, hydrolyzed proteins, lactose, etc. The carrier is preferably sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Generally, the ingredients are supplied either separately or mixed together in unit dosage form, for example, as a dry lyophilized powder or water free concentrate in a hermetically sealed container such as an ampule or sachette indicating the quantity of active agent. Where the composition is administered by injection, an ampule of sterile diluent can be provided so that the ingredients may be mixed prior to administration.

Peptides, derivatives and analogs thereof, and peptide mimetics that specifically bind an autoinducer can be produced by various methods known in the art, including, but not limited to solid-phase synthesis or by solution (Nakanishi et al., 1993, Gene 137:51–56; Merrifield, 1963, J. Am. Chem. Soc. 15:2149–2154; Neurath, H. et al., Eds., *The Proteins*, Vol II, 3d Ed., p. 105–237, Academic Press, New York, N.Y. (1976), incorporated herein in their entirety by reference).

Suitable carriers include lubricants and inert fillers such as lactose, sucrose, or cornstarch. In another embodiment, these compounds are tabletted with conventional tablet bases such as lactose, sucrose, or cornstarch in combination with binders like acacia, gum gragacanth, cornstarch, or gelatin; disintegrating agents such as cornstarch, potato starch, or alginic acid; a lubricant like stearic acid or magnesium stearate; and sweetening agents such as sucrose, lactose, or saccharine; and flavoring agents such as peppermint oil, oil of wintergreen, or artificial flavorings.

The autoinducer immunogenic conjugates or the autoinducer antibodies or binding portions thereof of the present invention may also be administered in injectable dosages by solution or suspension of these materials in a physiologically acceptable diluent with a pharmaceutical carrier. Such carriers include sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solution, and glycols such as polypropylene glycol or polyethylene glycol, are preferred liquid carriers, particularly for injectable solutions. To maintain sterility and prevent action of microorganisms, antibacterial and antifungal agents, such as parabens, chlorobutanol, phenol, ascorbic acid, thimerosal, and the like may be added to the carrier.

For use as aerosols, the immunogenic conjugates of the present invention, or antibodies or binding portions thereof according to the present invention, are alveolar lavage, lymph nodes, bone marrow, or other biopsied materials.

Toxicity and therapeutic efficacy of such molecules can be determined by standard pharmaceutical procedures in cell cultures or experimental animals, e.g., for determining the $LD_{50}$ (the dose lethal to 50% of the population).

The vaccines of the invention may be multivalent or univalent. Multivalent vaccines are made from immunoconjugation of multiple autoinducers with a carrier molecule.

In an embodiment, the autoinducer immunogenic conjugate vaccine formulation comprises an effective immunizing amount of the autoinducer immunogenic conjugate, preferably in combination with an immunostimulant; and a pharmaceutically acceptable carrier. As used in the present context, "immunostimulant" is intended to encompass any compound or composition which has the ability to enhance the activity of the immune system, whether it be a specific potentiating effect in combination with a specific antigen, or simply an independent effect upon the activity of one or more elements of the immune response. Immunostimulant compounds include but are not limited to mineral gels, e.g., aluminum hydroxide; surface active substances such as lysolecithin, pluronic polyols; polyanions; peptides; oil emulsions; alum, and MDP. Methods of utilizing these materials are known in the art, and it is well within the ability of the skilled artisan to determine an optimum amount of stimulant for a given autoinducer vaccine. More than one immunostimulant may be used in a given formulation. The immunogen may also be incorporated into liposomes, or conjugated to polysaccharides and/or other polymers for use in a vaccine formulation.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to a human. Associated with such container(s) can be a notice in the form prescribed by a governmental agency regulating the manufacture, use or sale of pharmaceuticals or biological products, which notice reflects approval by the agency of manufacture, use or sale for human administration.

5.4.2 Effective Dose

The compounds described herein can be administered to a patient at therapeutically effective doses to treat certain diseases caused by Gram negative bacteria that cause infectious diseases. A therapeutically effective dose refers to that amount of a compound sufficient to result in a healthful benefit in the treated subject.

The precise amount of immunogenic conjugate or antibody which specifically binds a BAI to be employed in the formulation will depend on the route of administration and the nature of the patient (e.g., age, size, stage/level of disease), and should be decided according to the judgment of the practitioner and each patient's circumstances according to standard clinical techniques. An effective immunizing amount is that amount sufficient to treat or prevent an infectious disease caused by a Gram negative bacteria that produces an autoinducer in a subject. Effective doses may also be extrapolated from dose-response curves derived from animal model test systems and can vary from 0.001 mg/kg to 100 mg/kg.

Toxicity and therapeutic efficacy of compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

Immunopotency of a composition can be determined by monitoring the immune response of test animals following immunization with the composition by use of any immunoassay known in the art. Generation of a humoral (antibody) response and/or cell-mediated immunity, may be taken as an indication of an immune response. Test animals may include mice, hamsters, dogs, cats, monkeys, rabbits, chimpanzees, etc., and eventually human subjects.

The immune response of the test subjects can be analyzed by various approaches such as: the reactivity of the resultant immune serum to the immunogenic conjugate, as assayed by known techniques, e.g., enzyme linked immunosorbent assay (ELISA), immunoblots, immunoprecipitations, etc.; or, by protection of immunized hosts from infection by the pathogen and/or attenuation of symptoms due to infection by the pathogen in immunized hosts as determined by any method known in the art, for assaying the levels of an infectious disease agent, e.g., the bacterial levels (for example, by culturing of a sample from the patient), etc. The levels of the infectious disease agent may also be determined by measuring the levels of the antigen against which the immunoglobulin was directed. A decrease in the levels of the infectious disease agent or an amelioration of the symptoms of the infectious disease indicates that the composition is effective.

The therapeutics of the invention can be tested in vitro, and then in vivo, for the desired therapeutic or prophylactic activity, prior to use in humans. For example, in vitro assays that can be used to determine whether administration of a specific therapeutic is indicated include in vitro cell culture assays in which appropriate cells from a cell line or cells cultured from a patient having a particular disease or disorder are exposed to or otherwise administered a therapeutic, and the effect of the therapeutic on the cells is observed.

Alternatively, the therapeutic may be assayed by contacting the therapeutic to cells (either cultured from a patient or from a cultured cell line) that are susceptible to infection by the infectious disease agent but that are not infected with the infectious disease agent, exposing the cells to the infectious disease agent, and then determining whether the infection rate of cells contacted with the therapeutic was lower than the infection rate of cells not contacted with the therapeutic. Infection of cells with an infectious disease agent may be assayed by any method known in the art.

In addition, the therapeutic can be assessed by measuring the level of the molecule against which the antibody is directed in the animal model or human subject at suitable time intervals before, during, or after therapy. Any change or absence of change in the amount of the molecule can be identified and correlated with the effect of the treatment on the subject. The level of the molecule can be determined by any method known in the art as described supra.

After vaccination of an animal to a Gram negative autoinducer using the methods and compositions of the present invention, any binding assay known in the art can be used to assess the binding between the resulting antibody and the particular molecule. These assays may also be performed to select antibodies that exhibit a higher affinity or specificity for the particular antigen.

5.5 Detection and Diagnostic Methods

Autoinducer antibodies or binding portions of the present invention are useful for detecting in a sample the presence of an autoinducer of a Gram negative bacteria. This detection method comprises the steps of providing an isolated antibody or binding portion thereof raised against an autoinducer of a Gram negative bacteria, adding to the isolated antibody or binding portion thereof a sample suspected of containing a quantity of the autoinducer, and detecting the presence of a complex comprising the isolated antibody or binding portion thereof bound to the autoinducer.

The antibodies or binding portions thereof of the present invention are also useful for detecting in a sample the presence of an autoinducer antagonist. This detection method comprises the steps of providing an isolated antibody or binding portion thereof raised against an autoinducer antagonist, adding to the isolated antibody or binding portion thereof a sample suspected of containing a quantity of the autoinducer antagonist, and detecting the presence of a complex comprising the isolated antibody or binding portion thereof bound to the autoinducer antagonist.

Immunoglobulins, particularly antibodies, (and functionally active fragments thereof) that bind a specific molecule that is a member of a binding pair may be used as diagnostics and prognostics, as described herein. In various embodiments, the present invention provides the measurement of a member of the binding pair, and the uses of such measurements in clinical applications. The immunoglobulins in the present invention may be used, for example, in the detection of an antigen in a biological sample whereby patients may be tested for aberrant levels of the molecule to which the immunoglobulin binds, and/or for the presence of abnormal forms of such molecules. By "aberrant levels" is meant increased or decreased relative to that present, or a standard level representing that present, in an analogous sample from a portion of the body or from a subject not having the disease. The antibodies of this invention may also be included as a reagent in a kit for use in a diagnostic or prognostic technique.

In an embodiment of the invention, an antibody of the invention that immunospecifically binds to an infectious disease agent may be used to diagnose, prognose or screen for an infectious disease associated with the expression of the antigen of the infectious disease agent.

In a preferred aspect, the invention provides a method of diagnosing or screening for the presence of an infectious disease agent, characterized by the presence of an autoinducer antigen of a Gram negative bacteria of said infectious disease agent, comprising measuring in a subject the level of immunospecific binding of an antibody to a sample derived from the subject, in which said antibody immunospecifically binds said antigen in which an increase in the level of said immunospecific binding, relative to the level of said immunospecific binding in an analogous sample from a subject not having the infectious disease agent, indicates the presence of said infectious disease agent.

The measurement of a molecule that is bound by an antibody can be valuable in detecting and/or staging diseases related to the molecule in a subject, in screening of such diseases in a population, in differential diagnosis of the physiological condition of a subject, and in monitoring the effect of a therapeutic treatment on a subject.

Examples of suitable assays to detect the presence of autoinducers or antagonists thereof include but are not limited to ELISA, radioimmunoassay, gel-diffusion precipitation reaction assay, immunodiffusion assay, agglutination assay, fluorescent immunoassay, protein A immunoassay, or immunoelectrophoresis assay.

The following assays are designed to detect molecules to which the antibodies immunospecifically bind. The tissue or cell type to be analyzed will generally include those which are known, or suspected, to express the particular molecule. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.). The isolated cells can be derived from cell culture or from a patient. The antibodies (or functionally active fragments thereof) useful in the present invention may, additionally, be employed histologically, as in immunofluorescence, immunohistochemistry, or immunoelectron microscopy, for in situ detection of the molecule. In situ detection may be accomplished by removing a histological specimen from a patient, such as paraffin embedded sections of affected tissues and applying thereto a labeled antibody of the present invention. The antibody (or functionally active fragment thereof) is preferably applied by overlaying the labeled antibody onto a biological sample. If the molecule to which the antibody binds is present in the cytoplasm, it may be desirable to introduce the antibody inside the cell, for example, by making the cell membrane permeable. Through the use of such a procedure, it is possible to determine not only the presence of the particular molecule, but also its distribution in the examined tissue. Using the present invention, those of ordinary skill will readily perceive that any of a wide variety of histological methods (such as staining procedures) can be modified in order to achieve such in situ detection of Gram negative bacteria autoinducers.

Immunoassays for the particular molecule will typically comprise incubating a sample, such as a biological fluid, a tissue extract, freshly harvested cells, or lysates of cultured cells, in the presence of a detectably labeled antibody and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled antibody. The solid phase support may then be washed with the buffer a second time to remove unbound antibody. The amount of bound label on solid support may then be detected by conventional means.

"Solid phase support or carrier" includes any support capable of binding an antigens or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given antibody may be determined according to well known methods. Those skilled in the art will be able to determine operative and optimal assay conditions for each determination by employing routine experimentation.

One of the ways in which an antibody can be detectably labeled is by linking the same to an enzyme and use in an enzyme immunoassay (EIA) (Voller, A., "The Enzyme Linked Immunosorbent Assay (ELISA)", 1978, *Diagnostic Horizons* 2:1–7, Microbiological Associates Quarterly Publication, Walkersville, Md.); Voller et al., 1978, *J. Clin. Pathol.* 31:507–520; Butler, 1981, *Meth. Enzymol.* 73:482–523; Maggio, E. (ed.), 1980, Enzyme Immunoassay, CRC Press, Boca Raton, Fla.,; Ishikawa et al., (eds.), 1981, Enzyme Immunoassay, Kgaku Shoin, Tokyo)). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other inmmunoassays. For example, by radioactively labeling the synthetic antibodies or fragments, it is possible to detect the protein that the antibody was designed for through the use of a radioimmunoassay (RIA) (see, for example, Weintraub, 1986, Principles of Radioimmunoassays, Seventh Training Course on Radioligand Assay Techniques, The Endocrine Society). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the synthetic antibody of the present invention. Bioluminescence is a type of chemiluminescence found in biological systems, in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An additional aspect of the present invention relates to diagnostic kits for the detection or measurement of autoinducer immuno. Kits for diagnostic use are provided, that comprise in one or more containers an anti-autoinducer antibody, and, optionally, a labeled binding partner to the antibody. Alternatively, the anti-autoinducer antibody can be labeled (with a detectable marker, e.g., a chemiluminescent, enzymatic, fluorescent, or radioactive moiety). Accordingly, the present invention provides a diagnostic kit comprising, an anti-autoinducer antibody and a control immunoglobulin. In a specific embodiment, one of the foregoing compounds of the container can be detectably labeled. A kit can optionally further comprise in a container a predetermined amount of an autoinducer recognized by the said anti-autoinducer antibody of the kit, for use as a standard or control.

The Examples set forth below are for illustrative purposes only and are not intended to limit, in any way, the scope of the present invention.

6 EXAMPLE

Synthesis

Preparation of Compound C

To a stirred solution of malonic acid mono tert-butylester A (419 mg, 90% purity, 2.35 mmol) and L-homoserine lactone hydrochloride B (324 mg, 2.35 mmol) in $CH_2Cl_2$ (15 mL) at room temperature was added sequentially $Et_3N$ (660 $\mu$L, 4.94 mmol) and Benzotriazol-1-yloxytris (dimethylamino)phosphonium hexfluorophosphate (BOP) (1.14 g, 2.58 mmol). After it was stirred for 3 hours (h), the mixture was concentrated, dissolved in EtOAc, washed with 1M HCl and saturated $NaHCO_3$, dried over $MgSO_4$, filtered, concentrated and the residual was chromatographed ($SiO_2$, Hexanes-EtOAc 1:1) to give C as a gum (571 mg, 2.35 mmol, ca. 100%).

$^1$H NMR (300 MHZ, $CDCl_3$): $\delta$ 7.85 (br s, 1H), 4.61 (m, 1H), 4.50 (m, 1H), 4.30 (m, 1H), 3.32 (s, 2H), 2.81 (m, 1H), 2.23 (m, 1H), 1.50 (s, 9H). IR (cm$^{-1}$): 1780, 1716, 1683. HRMS calculated for ($C_{11}H_{17}NO_5+NH_4^+$) at 261.1450, found at 261.1453.

Preparation of Compound D

To a stirred solution of C (122 mg, 500 $\mu$mol) in $CH_2Cl_2$ (5 mL) at room temperature was added TFA (385 $\mu$L, 5 mmol), and the resulting mixture was stirred for 4 h. The mixture was concentrated to give D as a gum (94 mg, 500 $\mu$mol, ca. 100%).

$^1$H NMR (300 MHZ, $CD_3CN$): $\delta$ 9.70 (br s, 1H), 7.46 (br s, 1H), 4.60 (m, 1H), 4.40 (m, 1H), 4.25 (m, 1H), 3.35 (s, 2H), 2.55 (m, 1H), 2.25 (m, 1H). IR (cm$^{-1}$): 1773; 1731; 1656. HRMS calculated for ($C_7H_9NO_5+NH_4^+$) at 205.0824, found at 205.0829.

Preparation of Compound 5

To a stirred solution of L-homoserine lactone (Sigma, 1.0 mmol) in 10 mL of water at room temperature was added the lithium or sodium salt of the fatty acid (1.0 mmol) followed by 1-(3-dimethylaminopropyl)-3-ethylcarbodiimide hydrochloride (Aldrich, 1.0 mmol). After 24 h, the resulting milky suspension was extracted several times with ethyl acetate. The combined extracts were dried ($MgSO_4$), filtered and the solvent removed in vacuo. The crude amides were then further purified by recrystallization from ethyl acetate/hexane.

$^1$H NMR ($CDCl_3$, $\delta$): 6.00 (bm, 1H), 4.46–4.69 (m, 2H), 4.25–4.34 (m, 1H), 2.94–2.93 (m, 1H), 2.26 (t, J=7 Hz, 2H), 2.10–2.28 (m, 1H), 1.63–1.68 (m, 2H), 1.27–1.31 (m, 10H), 09.89 (t, J=7 Hz, 3H). Anal. calcd for $C_{13}H_{23}NO_3$: C, 64.68; H, 9.62. Found: C, 64.77; H, 9.72. $[\alpha]^{25}_D+12°$ (c=2, $CHCl_3$), mp. 135–136° C.

Preparation of Compound 6

$^1$H NMR (acetone-d$_6$, +): 7.44 (bm, 1H), 4.55–4.65 (m, 1H), 4.21–4.40 (m, 2H), 2.49–2.57 (m, 1H), 2.16–2.27 (m, 3H), 1.53–1.60 (m, 2H), 1.26 (s, 16H), 0.85 (t, J=7 Hz, 3H). Anal. calcd for $C_{16}H_{29}NO_3$: C, 67.79; H, 10.33. Found: C, 67.87; H, 10.66.

Preparation of Compound 7

$^1$H NMR ($CDCl_3$, $\delta$): 6.00 (bd, 1H), 4.45–4.60 (m, 2H), 4.25–4.34 (m, 1H), 2.84–2.93 (m, 1H), 2.26 (t, J=7 Hz, 2H), 2.09–2.28 (m, 1H), 1.62–1.68 (m, 2H), 1.26–1.30 (m, 22H), 0.89 (t, J=7 Hz, 3H). Anal. calcd for $C_{19}H_{35}NO_3$: C, 70.01; H, 10.86. Found: C, 69.48; H, 11.20. $[\alpha]^{25}_D+12°$ (c=2, $CHCl_3$), mp. 138.139° C.

Preparation of Compound 8

To a stirred solution of Meldrums acid* (4.00 g; 27.8 mmol) and pyridine (5.62 mL; 69.4 mmol) in dry $CH_2Cl_2$ (12 mL) under $N_2$ at 0° C. was added freshly distilled decanoyl chloride (Aldrich, 5.76 mL; 27.8 mmol) dropwise. The reaction mixture gradually became deep red in color. After 1 h the mixture was allowed to warm up to room temperature for 1.5 h. At this point, the mixture was poured over crushed ice containing 20 mL of 2N HCl. The phases were separated and the aqueous layer further extracted with $CH_2Cl_2$. The combined organic extracts were dried ($MgSO_4$), filtered and concentrated in vacuo to give 3.882 g of crude beta-ketoester 8.

$^1$H NMR ($CDCl_3$, $\delta$): 3.03 (m, 2H), 1.75 (s, 6H), 1.62–1.70 (m, 2H), 1.25–1.35 (m, 12H), 0.89 (t, J=7 Hz, 3H).

*It is important to recrystallize the Meldrums acid from acetone before carrying out this experiment. The commercial material may be quite impure and adversely affect the purity of the final acylated product.

Preparation of Compound 10

The crude beta-ketoester from above was dissolved in 20 mL of dry methanol. The mixture was warmed to reflux under $N_2$. After 2.5 h, the mixture was allowed to cool to room temperature and the methanol removed in vacuo. The oily residue was chromatographed (Eluent: 7% ethyl acetate/hexane) to give 1.889 g (60%) of the beta-ketoester 9 as a mixture of keto-enol tautomers. To a stirred solution of the β-ketoester 9 (1.889 g; 8.3 mmol) in 20 mL of benzene at room temperature was added ethylene glycol (1.39 mL; 25 mmol) followed by 20 mg of p-TSA. The resulting mixture was then warmed to reflux (Dean-Stark). After 24.5 h, the mixture was allowed to cool to room temperature and washed with 10% $Na_2CO_3$ solution. The organic layer was then dried ($MgSO_4$), filtered and concentrated in vacuo. Flash chromatography on silica gel (eluent: 10% ethyl acetate/hexane) provided 1.926 g (85%) of the corresponding ketal 10 as a clear oil.

$^1$H NMR (CDCl$_3$, δ): 3.99 (m, 4H), 3.70 (s, 3H), 2.68 (s, 2H), 1.77–1.82 (m, 2H), 1.35–1.41 (m, 2H), 1.27 (s, 14H), 0.89 (t, J=7 Hz, 3H). anal. calcd. for $C_{15}H_{28}O_4$: C, 66.13; H, 10.38. Found: C, 66.30; H, 10.18.

Preparation of Compound 11

To a stirred solution of the ketal of 9 in methanol at room temperature was added LiOH solution (3.65 mL of 1.0 mmol/mL stock solution). The mixture was then warmed to reflux for 10 min. and then allowed to cool to room temperature. The solvent was then removed in vacuo to give crude carboxylate 10. The crude salt was then dissolved in 50 mL of water and 1-(3-dimethylaminopropyl)-3-ethylcarbodiimide hydrochloride (844 mg; 4.40 mmol) and L-homoserine lactone (556 mg; 4.04 mmol) were added sequentially. The mixture was allowed to stir for 6 h at room temperature and then the resulting thick white suspension extracted several times with ethyl acetate. The combined extracts were dried ($MgSO_4$), filtered and concentrated in vacuo to give a crude off-white solid. Recrystallization from ethyl acetate/hexane afforded 752 mg (60%) of the amide 11.

$^1$H NMR (CDCl$_3$, δ): 7.01 (d, J=6 Hz, 1H), 4.56–4.61 (m, 1H), 4.47 (t, J=9 Hz, 1H), 4.23–4.32 (m, 1H), 3.98–4.11 (m, 4H), 2.76–2.83 (m, 1H), 2.65 (s, 2H), 2.05–2.23 (m, 1H), 1.66–1.75 (m, 4H), 1.26–1.42 (m, 2H), 1.26 (s, 10H), 0.88 (t, 3=7 Hz, 3H). $[\alpha]^{25}_D$-16° (c=2, EtOH).

Preparation of Compound 13

To a stirred solution of the ketal 11 (330 mg; 0.97 mmol) in 2.0 mL of methanol at room temperature was added 0.1N HCl solution (2.0 mL). The resulting cloudy mixture was warmed to reflux for 1 h and then allowed to cool to room temperature. The majority of the methanol was then removed in vacuo and the remaining solution extracted several times with ethyl acetate. The combined extracts were dried ($MgSO_4$), filtered and concentrated in vacuo. Flash chromatography on silica gel (eluent: 70% ethyl acetate/hexane) afforded 122 mg (43%) of PAI 13 as a waxy white solid mp. 88–90° C.

$^1$H NMR (CDCl$_3$, δ): 7.70 (bm, 1H), 4.58–4.64 (m, 1H), 4.49 (t, J=9 Hz, 1H), 4.25–4.35 (m, 1H), 3.48 (s, 2H), 2.75–2.82 (m, 1H), 2.53 (t, J=6 Hz, 2H), 2.19–2.29 (m, 1H), 1.57–1.65 (m, H), 1.27 (s, H), 0.89 (t, J=9 Hz, 3H). Anal. calcd for $C_{16}H_{27}O_4N$: C, 64.60; H, 9.17. Found: C, 64.60; H, 9.44. $[\alpha]^{25}_D$-19° (c=2, EtOH).

Preparation of Compound 12

To a stirred solution of the ester 10 (1.00 g; 3.67 mmol) in 5.0 mL of methanol at room temperature was added LiOH solution (3.55 mL of 1.0 mmol/mL stock solution). The mixture was then warmed to reflux for 15 min. and then allowed to cool to room temperature. The solvent was then removed in vacuo, the residue redissolved in 40 mL of water and L-homocysteine thiolactone hydrochloride (473 mg; 3.08 mmol) and 1-(3-dimethylaminopropyl)-3-ethylcarbodiimide hydrochloride (590 mg; 3.08 mmol) were added sequentially. The resulting mixture was allowed to stir for 19.5 h at room temperature and then extracted several times with ethyl acetate. The combined extracts were dried ($MgSO_4$), filtered and concentrated in vacuo. Flash chromatography on silica gel (eluent: 85% ethyl acetate/hexane) provided 585 mg. (64%) of the thiolactone-amide 12 as a white solid.

$^1$H NMR (CDCl$_3$, δ): 6.92 (bd, 1H), 4.57–4.62 (m, 1H), 3.98–4.12 (m, 4H), 3.24–3.40 (m, 2H), 2.87–2.93 (m, 1H), 2.65 (s, 2H), 1.92–2.00 (m, 1H), 1.66–1.75 (m, 2H), 1.32–1.40 (m, 2H), 1.27 (s, 12H), 0.89 (t, J=7 Hz, 3H).

Preparation of Compound 14

To a stirred solution of the ketal 12 (487 mg; 1.36 mmol) in 12.0 mL of methanol at room temperature was added 0.1N HCl solution (7.0 mL). The resulting cloudy mixture was warmed to reflux for 30 min. and then allowed to cool to room temperature. The majority of the methanol was then removed in vacuo and the remaining solution extracted several times with ethyl acetate. The combined extracts were dried ($MgSO_4$), filtered and concentrated in vacuo. Flash chromatography on silica gel (eluent: 85% ethyl acetate/hexane) provided 323 mg (76%) of the keto-amide 14 as a white solid, mp. 86–88° C.

$^1$H NMR (CDCl$_3$, δ): 7.51 (bd, 1H), 4.60 (m, 1H), 3.47 (s, 2H), 3.24–3.44 (m, 2H), 2.82–2.90 (m, 1H), 2.54 (t, J=7 Hz, 2H), 1.98–2.09 (m, 1H), 1.57–1.61 (m, 2H), 1.27 (s, 12H), 0.89 (t, J=7 Hz, 3H). Anal. calcd for $C_{16}H_{27}NO_3S$: C, 61.29; H, 8.70. Found: C, 61.21; H, 8.75. $[\alpha]^{25}_D$-19° (c=2, EtOH).

Preparation of Compound 15

To a stirred solution of PAI 13 (70 mg; 0.24 mmol) in 3.0 mL of dry methanol under $N_2$ at -15° C. was added sodium borohydride (10 mg; 0.26 mmol). After 1 h, another 10 mg of sodium borohydride was added and stirring allowed to continue for another hour. At this point, the mixture was quenched with 1 mL of acetone and allowed to warm to room temperature. The solvent was removed in vacuo, the residue redissolved in $CH_2Cl_2$ and washed with water. The organic layer was then dried ($MgSO_4$), filtered and concentrated in vacuo. The crude solid was recrystallized from ethyl acetate/hexane to give 39 mg. (55%) of the hydroxy-amide 15 as a mixture of 2 diastereomers.

$^1$H NMR (CDCl$_3$, δ): 6.48–6.60 (bm, 1H), 4.46–4.64 (M, 2H), 4.27–4.38 (m, 1H), 4.00–4.06 (m, 1H), 2.81–2.90 (m, 1H), 2.08–2.52 (m, 5H), 1.39–1.58 (m, 2H), 1.28 (s, 12H).

Preparation of Compound 17

To a stirred solution of the oxazolidinone 16 (Fluka, 388 mg; 3.0 mmol) in 10 mL of dry THF under $N_2$ at -78° C. was added n-BuLi solution (1.38 mL of 2.4 mmol/mL solution) dropwise. At the end of the addition, the mixture was warmed to 0° C. for 10 min., quenched with decanoyl chloride (0.81 mL; 3.9 mmol) and stirred for an additional 30 min. at this temperature. At this point, the mixture was quenched with 2.0 mL of saturated $NaHCO_3$ solution and the solvent removed in vacuo. The residue was taken up into $CH_2Cl_2$ and washed with 20% $K_2CO_3$ solution. The organic layer was then dried (MgSO$_4$), filtered and the solvent removed in vacuo. Flash chromatography on silica gel (eluent: 35% ethyl acetate/hexane) provided 740 mg. (87%) of oily oxazolidinone 17.

$^1$H NMR (CDCl$_3$, δ): 4.43–4.48 (m, 1H), 4.20–4.31 (m, 2H), 2.83–3.03 (m, 2H), 2.36–2.42 (m, 1H), 1.62–1.69 (m, 2H), 1.28–1.33 (m, 12H), 0.88–0.94 (m, 9H), Anal. calcd for C$_{16}$H$_{29}$O$_3$N: C, 67.79; H, 10.33. Found: C, 67.87; H, 10.59. $[\alpha]^{25}_{D+}69°$ (c=2, EtOH).

Preparation of Compound 21

To a stirred solution of trans-4-decanal (2.00 g; 13.0 mmol) and sulfamic acid (3.78 g; 38.9 mmol) in 80 mL of 3:1 THF:H$_2$O at 0° C. was added NaClO$_2$ solution (1.41 g; 15.6 mmol dissolved in 10 mL of water) dropwise. At the end of the addition, the mixture was allowed to warm to room temperature for 10 min. At this point, most of the THF was then removed in vacuo. The resulting mixture was extracted several times with CH$_2$Cl$_2$. The combined extracts were dried (MgSO$_4$), filtered and concentrated in vacuo. The residue was diluted with 10 mL of hexane, filtered and finally concentrated in vacuo to give 2.342 g of crude oily acid 18. To a stirred solution of the crude acid (2.342 g) in 50 mL of dry CH$_2$Cl$_2$ under N$_2$ at room temperature was added 2 drops of DMF followed by oxalyl chloride (1.56 mL; 17.9 mmol) dropwise. After 30 min., gas evolution had ceased and the solvent was removed in vacuo to provide the crude acid chloride 19. Crude 19 was then redissolved in 30 mL of CH$_2$Cl$_2$ and Meldrums acid (1.99 g; 13.8 mmol) was added. The mixture was cooled to 0° C. and pyridine (2.79 mL; 34.5 mmol) was dropwise. After the addition was complete, the mixture was allowed to warm to room temperature for 1.5 h then diluted with CH$_2$Cl$_2$ and washed with 10% KHSO$_4$ solution. The organic layer was then dried (MgSO$_4$), filtered and concentrated in vacuo. The residue was then dissolved in 30 mL of methanol and heated to reflux for 1 h, cooled and the solvent removed in vacuo. The oily residue was chromatographed on silica gel (eluent: 8% ethyl acetate/hexane) to give 558 mg (18%) of the beta-ketoester 21 as a clear oil.

Keto tautomer: $^1$H NMR (CDCl$_3$, δ): 5.37–4.58 (m, 2H), 3.76 (s, 3H), 3.47 (s, 2H), 2.62 (t, J=7 Hz, 2H), 2.27–2.35 (m, 3H), 1.94–2.01 (m, 2H), 1.23–1.38 (m, 6H), 0.90 (s, 3H).

Preparation of Compound 22

To a stirred solution of the beta-ketoester in benzene at room temperature was added ethylene glycol (0.64 mL; 11.4 mmol) followed by a trace of p-TSA. The mixture was then warmed to reflux Dean-Stark). After 4 h, another 0.64 mL of ethylene glycol was added. After a total of 23 h, the mixture was allowed to cool to room temperature and washed with 10% Na$_2$CO$_3$ solution. The organic layer was then dried (MgSO$_4$), filtered and concentrated in vacuo. Flash chromatography on silica gel (eluent: 8% ethyl acetate/hexane provided 513 mg (50%) of the ketal intermediate 22 together with 152 mg (18%) of recovered beta-ketoester 21.

$^1$H NMR (CDCl$_3$, δ): 5.39–5.49 (m, 2H), 3.99–4.01 (4H), 3.71 (s, 3H), 2.69 (s, 2H), 1.86–2.15 (m, 7H), 1.29–1.37 (m, 6H), 0.90 (t, J=7 Hz, 3H).

Preparation of Compound 24

To a stirred solution of the ketal (450 mg; 1.66 mmol) in 4.0 mL of methanol at room temperature was added LiOH solution (1.66 mL of 1.0 M stock solution). The mixture was then warmed to reflux for 15 min. and then allowed to cool. The solvent was removed in vacuo and the crude carboxylate redissolved in 20 mL of water. To this solution was added L-homoserine lactone hydrochloride (251 mg; 1.83 mmol) followed by 1-(3-dimethylaminopropyl)-3-ethylcarbodiimide hydrochloride (350 mg; 1.83 mmol) and the mixture allowed to stir for 6 h at room temperature. At this point, the mixture was extracted several times with ethyl acetate. The combined extracts were dried (MgSO$_4$), filtered and concentrated in vacuo to give 531 mg of crude amide 24.

$^1$H NMR (CDCl$_3$, δ): 7.00 (d, J=6 Hz, 1H), 5.38–5.44 (m, 2H), 4.55–4.65 (m, 1H), 4.45–4.51 (m, 1H), 4.28–4.31 (m, 1H), 3.99–4.12 (m, 4H), 2.79–2.83 (m, 1H), 2.67 (s, 2H), 1.74–2.19 (m, 7H), 1.29–1.36 (m, 6H), 0.89 (t, J=7 Hz, 3H).

Preparation of Compound 25

The crude amide 24 was dissolved in 4.0 mL of methanol at room temperature and 3.0 mL of 0.1 N HCl solution was added. The resulting mixture was warmed to reflux for 1 h, cooled to room temperature and the majority of the methanol removed in vacuo. The remaining aqueous phase was extracted several times with ethyl acetate. The combined extracts were dried (MgSO$_4$), filtered and concentrated in vacuo. Flash chromatography on silica gel (eluent: 75% ethyl acetate/hexane) gave 175 mg (36%) of the unsaturated keto-amide 25, mp. 92–93° C.

$^1$H NMR (CDCl$_3$, δ): 7.70 (d, J=4.3 Hz, 1H), 5.32–5.50 (m, 2H), 4.56–4.65 (m, 1H), 4.46–4.52 (m, 1H), 4.25–4.33 (m, 1H), 3.48 (s, 2H), 2.72–2.81 (m, 1H), 2.58–2.63 (m, 2H), 2.17–2.32 (m, 3H), 1.93–1.98 (m, 2H), 1.25–1.38 (m, 6H), 0.89 (t, J=7 Hz, 3H). $[\alpha]^{25}_D -23°$ (c=2, EtOH).

Preparation of Compound 27

Prepared by coupling of the aminolactam 26 (129 mg; 0.94 mmol) and the lithium salt derived from the ester 10 (278 mg; 1.02 mmol) in water (2.0 mL) in the presence of carbodiimide 4 (180 mg; 0.94 mmol) according to the procedure used for the preparation of compound 11. The crude product (293 mg) was then dissolved in 7.0 mL of methanol and 3.0 mL of 0.1 N HCl was added and the mixture heated to reflux for 1 h and then allowed to cool to room temperature and then processed as for compound 14. The crude solid product was recrystallized from ethyl acetate/hexane to give 150 mg (54%) of amide 27, mp. 158–160° C.

$^1$H NMR (CDCl$_3$, δ): 7.60 (bm, 1H), 6.45 (bm, 1H), 4.45 (M, 1H), 3.47 (s, 2H), 3.38–3.42 (m, 2H), 2.69–2.77 (m, 1H), 2.55 (t, J=7 Hz, 2H), 1.96–2.04 (m, 1H), 1.58–1.61 (m, 2H), 1.27 (s, 12H), 0.89 (t, J=7 Hz, 3H).

Preparation of Compound 29

A solution of maleic anhydride (12.2 mg, 0.125 mmol) in dichloromethane (0.2 mL) was added to a solution of DL homoserine lactone (12.6 mg, 0.125 mmol) in dichloromethane (0.1 mL). As the mixture was stirred, a white precipitate formed rapidly, became oily over 10 min, then became a granular solid over the next 10 min. Stirring was continued for a total of 75 min, and the mixture was then diluted with di-isopropyl ether (2 mL) and the solid was removed by filtration to give N-maleoylhomoserine lactone (20 mg, 81%).

$^1$H NMR (DMSO) 13.3 (br s, 1 H), 9.12 (br d, J=8.8 Hz, 1 H), 6.30, 6.24 (2 d, J=12.2 Hz, 1 H each), 4.64 (ddd, J=10.5, 9.1, 7.9 Hz, 1 H), 4.36 (ddd, J=8.8, 8.8, 1.9 Hz, 1 H), 4.23 (ddd, I=10.5, 8.7, 6.5 Hz, 1 H), 2.43 (dddd, J=12.2, 9.1, 6.4, 1.9 Hz, 1 H), 2.19 (dddd, J=12.2, 8.8, 8.7, 7.9 Hz, 1 H). 13C NMR (DMSO) 174.8(s), 166.5(s), 164.8(s), 131.7(d), 130.2(d), 65.5(t), 48.2(d), 21.8(t).

7. EXAMPLE

Production of BAI Antibodies

Production of anti-autoinducer antibodies and experimental in vivo therapeutic evaluation of said anti-autoinducer antibodies is described in the sections that follow. Specifically, antibodies were made to immunogenic conjugates containing PAI-1 covalently bound to bovine serum albumin, however, one of ordinary skill in the art will easily recognize that other autoinducer molecules and additional conjugates may be used in a similar procedure to produce various combinations of immunogenic conjugates and antibodies that recognize said immunogenic conjugates. One of ordinary skill in the art will also recognize that additional animal models can be used to assay the therapeutic and diagnostic effectiveness of the anti-autoinducer antibodies.

7.1 PAI's Role in Virulence

The role of PAI-1 and PAI-2 in colonization of *Pseudomonas aeruginosa* in neonatal mice was examined. BALB/cBy, mice 7–10 days old, were inoculated intranasally with approximately $10^8$ CFU of either wild type or deletion mutants of *P. aeruginosa*. The lasI gene product is a synthase required for PAI-1 production and the rhlI gene product is required for production of PAI-2 (Passador et al., 1996, J. Bact. 178:5995–6000). The deletion strains were: PAO1, wild type; PAO-JP2, bearing a double deletion of lasI/rhlI; PAO-JP1, bearing a lasI deletion; and PAO-JP2/pJPP42, bearing a double deletion lasI/rhlI but carrying a complementing plasmid expressing both lasI and rhlI. Bacterial suspensions of these strains were given in 2 μl aliquots directly into the mouse nares until a total of 10 μl had been administered. Twenty-four hours after challenge, mice were sacrificed, and the right lung cultured for bacterial load and the left lung fixed in 10% buffered formalin for histological analysis. Pneumonia was defined as ≧100 CFU of *Pseudomonas aeruginosa* in the lung. Bacteremia was defined as any bacteria cultured from the spleen.

The results indicate that mice inoculated with strain PAO-JP1, which does not produce PAI-1, exhibited a significant decrease in the rates of pneumonia, bacteremia, and mortality in comparison to PAO1 (FIG. 1). Moreover, mice inoculated with strain PAO-JP2, which produces neither PAI-1 nor PAI-2, exhibited an additional decrease in the rates of pneumonia, bacteremia, and mortality over the already reduced infection rate of PAO1. In sharp contrast, mice inoculated with *Pseudomonas aeruginosa* JP2/pJPP42, which produces PAI-1 and PAI-2 by virtue of a genetically complementing plasmid, exhibited pneumonia, bacteremia, and mortality rates comparable to wild type, PAO1 (FIG. 1).

7.2 Anti-PAI Polyclonal Antibodies

The *Pseudomonas aeruginosa* autoinducer PAI-1 (structure on page 16) and Compound D (structure on page 9) were separately conjugated to bovine serum albumin (BSA). These conjugates were used to immunize different BALB/c mice. Initial injections of 50 μg of conjugate were administered subcutaneously in Freund's complete adjuvant and two weeks later were boosted with a second subcutaneous injection in Freund's incomplete adjuvant. After two additional weeks, mice were tail bled and serum was isolated. A sandwich enzyme-linked immunosorbent assay (ELISA) utilizing a PAI-1 ovalbumin (OVA) conjugate was used to test for the production of specific serum antibodies that recognize autoinducers. Serum samples with an optical density (OD) that was five to ten fold higher than serum from mice immunized with BSA only were considered positive.

7.3 Neutralization of PAI with Antibodies

In Vitro neutralization of PAI-1 with anti-PAI-1 polyclonal antibodies. Immune serum, collected in Section 7.2, were tested for neutralization of PAI-1 in an in vitro bioassay. The *E. coli* MG4 strain, containing the lysogen $\lambda I_14$ (a lasI/lasZ transcriptional fusion) and pPCS1 (a plasmid expressing lasR), was used as a positive control to detect the presence of PAI-1. Normally, when PAI-1 is added to cultures it can bind LasR, the PAI-1 specific transcriptional activator protein, and form a complex that is able to induce transcription of the lasI/lasZ fusion protein. The production of β-galactosidase in this system is a quantitative and direct measure of the activation induced by PAI-1. The expression construct, $\lambda I_14$-MG4 (pPCS1), has been shown to have half-maximal expression at PAI-1 concentrations of 100 pM and can be activated at PAI-1 concentrations as low as 10 pM (Seed et al., 1995, J. Bacteriol. 177:654–59, which is hereby incorporated by reference).

A test sample containing 100 pM of PAI-1 was preincubated for one hour at 37° C. with a 1:10 dilution of serum from mice immunized with a PAI-1 conjugate or a Compound D conjugate (both contain anti-PAI-1 polyclonal antibodies). Control samples containing 100 pM PAI-1 were incubated at 37° C. for one hour with a 1:10 dilution of preimmune serum or an equal volume of PBS. Following preincubation, the samples were tested in an *E. coli* bioassay using $\lambda I_14$-MG4 (pPCS1). When the bacteria in each sample reached an OD600 of 0.8–1.0 the samples were assayed for the production of β-galactosidase which was expressed as Miller Units of activity. The test samples preincubated with serum from immune mice displayed a 70% reduction in β-galactosidase production as compared to control sample preincubated with nonimmune serum (FIG. 2). These results indicate that PAI-1 conjugates or related conjugates (Compound D) can induce the production of polyclonal antibodies that can react with PAI-1 and inhibit its interaction with LasR.

Mice immunized with the PAI-1 conjugate were used to produce monoclonal antibodies. These antibodies were screened using an ELISA utilizing a PAI-1/OVA conjugate. Positive clones were tested in a *Pseudomonas aeruginosa* bioassay. PAO-JP2 (bearing the lasI/rhlI double deletion) produces no PAI-1 but retains the ability to produce LasR. When PAI-1 is added exogenously, it can bind to LasR and induce the transcription of lasI. Test samples containing 40 nM PAI-1 (the concentration that stimulates half-maximal activity in this assay) were preincubated at 37° C. with anti-PAI-1 monoclonal antibody (618.4). Control samples containing 40 nm PAI-1 were preincubated at 37° C. with an equal volume of PBS. Following preincubation, the samples were tested in a *Pseudomonas aeruginosa* bioassay using PAO-JP2 containing a plasmid with a lasI/LacZ fusion. When the bacteria reached on $OD_{600}$ of 0.8–1.0, the samples were assayed for the production of β-galactosidase, which was expressed as Miller Units of activity. The test sample preincubated with anti-PAI-1 monoclonal antibody 618.4 displayed an 80% reduction in the production of β-galactosidase as compared to the control sample (FIG. 3). These results indicate that in *Pseudomonas aeruginosa* antibodies specific for PAI-1 can inhibit PAI-1 activation of LasR and transcription of other genes that are regulated by LasR/PAI-1.

Although the invention has been described in detail for the purposes of illustration, it is understood that such detail is solely for that purpose, and variations can be made therein by those skilled in the art without departing from the spirit and scope of the invention which is defined by the following claims.

What is claimed is:

1. An isolated antibody or fragment thereof which specifically binds an autoinducer of or produced by a Gram negative bacterium.

2. The isolated antibody or fragment thereof of claim 1 in which the autoinducer is a compound of Formula (I):

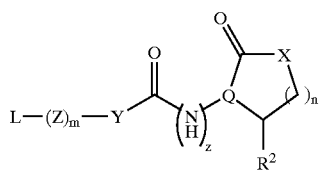

(I)

where X is O, S, N—($C_1$–$C_6$) alkyl, $NR^2$, N-phenyl; Y is $C_1$–$C_6$ straight or branched alkyl, $C_1$–$C_6$ straight or branched alkenyl, $C_1$–$C_6$ straight or branched alkynyl; Z is C=O, C=S, CHOH, C=N—$NR^1$, C=N—OH, $C_1$–$C_8$ straight or branched alkyl, $C_1$–$C_8$ straight or branched alkenyl, $C_1$–$C_8$ straight or branched alkynyl; L is $C_1$–$C_8$ straight or branched alkyl, $C_1$–$C_{18}$ straight or branched alkenyl, $C_1$–$C_{18}$ straight branched alkynyl, or —$CO_2H$, —$CO_2R^1$, —CHO, —C≡N, —N=C=C, —N=C=S, OH, $OR^1$, —CH=CH—$CH_2$Br, —CH=CH—$CH_2$Cl, —SAc or SH, where $R^1$ is $C_1$–$C_6$ straight or branched alkyl, m is 0 or 1; z is 0 or 1; $R^2$ is H, $C_1$–$C_6$ straight or branched alkyl, $C_1$–$C_6$ straight or branched alkenyl or $C_1$–$C_6$ straight or branched alkynyl, or $CO_2H$; and Q is CH or N; and n is 0–3 with the proviso that when n is 0, X is N—($C_1$–$C_6$ alkyl) or N-phenyl.

3. The isolated antibody or fragment thereof of claim 1 which is a monoclonal antibody.

4. The isolated antibody or fragment thereof of claim 1 in which the autoinducer comprises N-(3-oxododecanoyl)-L-homoserine lactone, N-(butanoyl)-L-homoserine lactone, N-hexanoyl-homoserine lactone, N-(3-oxohexanoyl)-homoserine lactone, N-β(hydroxybutyryl)-homoserine lactone, N-(3-oxooctanoyl)-L-homoserine lactone, or N-(3R-hydroxy-cis-tetradecanoyl)-L-homoserine lactone.

5. The isolated antibody or fragment thereof of claim 4 in which the autoinducer is N-(3-oxododecanoyl)-L-homoserine lactone or N-(butanoyl)-L-homoserine lactone.

6. The isolated antibody or fragment thereof of claim 1 in which the autoinducer is covalently conjugated or non-covalently bound to a carrier molecule.

7. The isolated antibody or fragment thereof of claim 6 in which the carrier molecule is selected from the group consisting of bovine serum albumin, chicken egg ovalbumin, keyhole limpet hemocyanin, tetanus toxoid, diphtheria toxoid, and thyroglobulin.

8. The isolated antibody or fragment thereof of claim 1 in which the autoinducer is produced by a Gram negative bacterium selected from the group consisting of *Aeromonas hydrophila*, *Agrobacterium tumefaciens*, *Burkholderia cepacia*, *Chromobacterium violaceum*, *Enterobacter agglomerans*, *Erwinia stewarti*, *Erwinia carotovora*, *Escherichia coli*, *Nitrosomas europea*, *Photobacterium fiseheri*, *Pseudomonas aeruginosa*, *Pseudomonas aureofaciens*, *Rhizobium leguminosarum*, *Serratia liquefaciens*, and *Vibrio harveyi*.

9. A diagnostic kit comprising an antibody which specifically binds an autoinducer of a Gram negative bacterium of a compound of Formula (I):

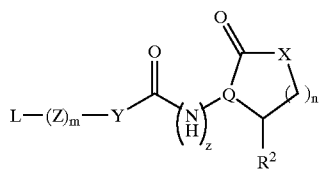

(I)

where X is O, S, N—($C_1$–$C_6$) alkyl, $NR^2$, N-phenyl; Y is $C_1$–$C_6$ straight or branched alkyl, $C_1$–$C_6$ straight or branched alkenyl, $C_1$–$C_6$ straight or branched alkynyl; Z is C=O, C=S, CHOH, C=N—$NR^1$, C=N—OH, $C_1$–$C_8$ straight or branched alkyl, $C_1$–$C_8$ straight or branched alkenyl, $C_1$–$C_8$ straight or branched alkynyl; L is $C_1$–$C_{18}$ straight or branched alkyl, $C_1$–$C_{18}$ straight or branched alkenyl, $C_1$–$C_{18}$ straight branched alkynyl, or —$CO_2H$, —$CO_2R^1$, —CHO, —C≡N, —N=C=O, —N=C=S, OH, $OR^1$, —CH=CH—$CH_2$Br, —CH=CH—$CH_2$Cl, —SAc or SH, where $R^1$ is $C_1$–$C_6$ straight or branched alkyl, m is 0 or 1; z is 0 or 1; $R^2$ is H, $C_1$–$C_6$ straight or branched alkyl, $C_1$–$C_6$ straight or branched alkenyl or $C_1$–$C_6$ straight or branched alkynyl, or $CO_2H$; and Q is CH or N; and n is 0–3 with the proviso that when n is 0, X is N—($C_1$–$C_6$ alkyl) or N-phenyl.

10. A pharmaceutical composition comprising an antibody or fragment thereof which specifically binds an autoinducer produced by a Gram negative bacterium; and a pharmaceutically acceptable carrier.

11. The pharmaceutical composition of claim 10 in which the autoinducer is a compound of Formula (I):

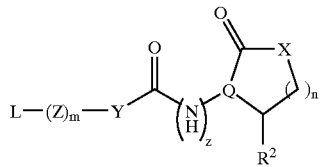

(I)

where X is O, S, N—($C_1$–$C_6$) alkyl, $NR^2$, N-phenyl; Y is $C_1$–$C_6$ straight or branched alkyl, $C_1$–$C_6$ straight or branched alkenyl, $C_1$–$C_6$ straight or branched alkynyl; Z is C=O, C=S, CHOH, C=N—$NR^1$, C=N—OH, $C_1$–$C_8$ straight or branched alkyl, $C_1$–$C_8$ straight or branched alkenyl, $C_1$–$C_8$ straight or branched alkynyl; L is $C_1$–$C_{18}$ straight or branched alkyl, $C_{1–C_{18}}$ straight or branched alkenyl, $C_1$–$C_{18}$ straight branched alkynyl, or —$CO_2H$, —$CO_2R^1$, —CHO, —C≡N, —N=C=O, —N=C=S, OH, $OR^1$, —CH=CH—$CH_2$Br, —CH=CH—$CH_2$Cl, —SAc or SH, where $R^1$ is $C_1$–$C_6$ straight or branched alkyl, m is 0 or 1; z is 0 or 1; $R^2$ is H, $C_1$–$C_6$ straight or branched alkyl, $C_1$–$C_6$ straight or branched alkenyl or $C_1$–$C_6$ straight or branched alkynyl, or $CO_2H$; and Q is CH or N; and n is 0–3 with the proviso that when n is 0, X is N—($C_1$–$C_6$ alkyl) or N-phenyl; and a pharmaceutically acceptable carrier.

12. The pharmaceutical composition of claim 10 in which the antibody is a monoclonal antibody.

13. The pharmaceutical composition of claim 10 in which the autoinducer comprises N-(3-oxododecanoyl)-L-homoserine lactone, N-(butanoyl)-L-homoserine lactone, N-hexanoyl-homoserine lactone, N-(3-oxohexanoyl)-homoserine lactone, N-β(hydroxybutyryl)-homoserine lactone, N-(3-oxooctanoyl)-L-homoserine lactone, or N—(3R-hydroxy-cis-tetradecanoyl)-L-homoserine lactone.

14. The pharmaceutical composition of claim 10 in which the autoinducer is N-(3-oxododecanoyl)-L-homoserine lactone or N-(butanoyl)-L-homoserine lactone.

15. The pharmaceutical composition of claim 10 in which the autoinducer is covalently conjugated or non-covalently bound to a carrier molecule.

16. The pharmaceutical composition of claim 15 in which the carrier molecule is selected from the group consisting of bovine serum albumin, chicken egg ovalbumin, keyhole limpet hemocyanin, tetanus toxoid, diphtheria toxoid, and thyroglobulin.

17. The pharmaceutical composition of claim 10 in which the autoinducer is produced by a Gram negative bacterium selected from the group consisting of *Aeromonas hydrophila, Agrobacterium tumefaciens, Burkholderia cepacia, Chromobacterium violaceum, Enterobacter agglomerans, Erwinia stewarti, Erwinia carotovora, Escherichia coli, Nitrosomas europea, Photobacterium fischeri, Pseudomonas aeruginosa, Pseudomonas aureofaciens, Rhizobium leguminosarum, Serratia liquefaciens,* and *Vibrio harveyi*.

\* \* \* \* \*